(12) United States Patent
Glukhovsky

(10) Patent No.: US 8,364,277 B2
(45) Date of Patent: Jan. 29, 2013

(54) METHODS AND APPARATUS FOR IMPLANTING ELECTRONIC IMPLANTS WITHIN THE BODY

(75) Inventor: Arkady Glukhovsky, Santa Clarita, CA (US)

(73) Assignee: Bioness Inc., Valencia, CA (US)

( * ) Notice: Subject to any disclaimer, the term of this patent is extended or adjusted under 35 U.S.C. 154(b) by 1124 days.

(21) Appl. No.: 11/972,402

(22) Filed: Jan. 10, 2008

(65) Prior Publication Data

US 2009/0182403 A1    Jul. 16, 2009

(51) Int. Cl.
*A61N 1/372* (2006.01)

(52) U.S. Cl. .............. 607/62; 607/2; 600/547; 600/585; 606/108; 606/129; 606/172; 606/185; 128/898; 128/899

(58) Field of Classification Search .................. None
See application file for complete search history.

(56) References Cited

U.S. PATENT DOCUMENTS

| | | |
|---|---|---|
| 2,725,629 A | 12/1955 | Todhunter |
| 3,204,637 A | 9/1965 | Frank et al. |
| 3,426,748 A | 2/1969 | Bowers |
| 4,166,469 A | 9/1979 | Littleford |
| 4,306,560 A | 12/1981 | Harris |
| 4,898,183 A | 2/1990 | Kuzma |
| 4,958,901 A | 9/1990 | Coombs |
| 5,003,990 A | 4/1991 | Osypka |
| 5,170,787 A | 12/1992 | Lindegren |
| 5,292,309 A | 3/1994 | Van Tassel et al. |
| 5,300,106 A | 4/1994 | Dahl et al. |
| 5,304,218 A | 4/1994 | Alferness |
| 5,439,464 A | 8/1995 | Shapiro |
| 5,443,493 A | 8/1995 | Byers et al. |
| 5,586,553 A | 12/1996 | Halili et al. |
| 5,667,514 A | 9/1997 | Heller |
| 5,706,814 A * | 1/1998 | Nonomura .................... 600/420 |
| 5,782,841 A | 7/1998 | Ritz et al. |
| 5,797,923 A | 8/1998 | Aiyar et al. |
| 5,984,890 A | 11/1999 | Gast et al. |
| 6,051,017 A | 4/2000 | Loeb et al. |
| 6,119,044 A | 9/2000 | Kuzma |
| 6,132,456 A | 10/2000 | Sommer et al. |

(Continued)

FOREIGN PATENT DOCUMENTS

WO    WO 00/40955    7/2000

OTHER PUBLICATIONS

International Search Report and Written Opinion for PCT/US08/83084, mailed Jan. 9, 2009.

(Continued)

*Primary Examiner* — Kennedy J Schaetzle
(74) *Attorney, Agent, or Firm* — Cooley LLP

(57) ABSTRACT

An apparatus includes an implant delivery device configured to deliver an implant into a body. The implant delivery device includes a target member, an insertion member and an electronic circuit system. The target member has a distal end portion configured to be disposed within the body adjacent a target location. The insertion member is movably coupled to the target member. A distal end portion of the insertion member is configured to be disposed within the body and selectively coupled to the implant. The electronic circuit system is configured to produce an electronic signal in proportion to a distance between the distal end portion of the target member and the distal end portion of the insertion member when the target member and the insertion member are disposed within the body.

24 Claims, 16 Drawing Sheets

U.S. PATENT DOCUMENTS

| | | |
|---|---|---|
| 6,149,657 A | 11/2000 | Kuzma |
| 6,185,464 B1 | 2/2001 | Bonner et al. |
| 6,304,785 B1 | 10/2001 | McCreery et al. |
| 6,304,787 B1 | 10/2001 | Kuzma et al. |
| 6,332,089 B1 * | 12/2001 | Acker et al. .................. 600/424 |
| 6,337,994 B1 * | 1/2002 | Stoianovici et al. .......... 600/547 |
| 6,360,750 B1 | 3/2002 | Gerber et al. |
| 6,379,346 B1 | 4/2002 | McIvor et al. |
| 6,505,075 B1 | 1/2003 | Weiner |
| 6,530,929 B1 | 3/2003 | Justis et al. |
| 6,582,441 B1 | 6/2003 | He et al. |
| 6,605,094 B1 | 8/2003 | Mann et al. |
| 6,697,677 B2 | 2/2004 | Dahl et al. |
| 6,829,508 B2 | 12/2004 | Schulman et al. |
| 6,904,324 B2 | 6/2005 | Bishay |
| 6,968,238 B1 | 11/2005 | Kuzma |
| 6,971,393 B1 | 12/2005 | Mamo et al. |
| 6,999,819 B2 | 2/2006 | Swoyer et al. |
| 7,018,384 B2 | 3/2006 | Skakoon |
| 7,050,858 B1 | 5/2006 | Kuzma et al. |
| 7,151,965 B2 | 12/2006 | Osypka |
| 7,155,287 B2 | 12/2006 | Gavronsky |
| 7,200,444 B2 | 4/2007 | Gavronsky et al. |
| 7,289,843 B2 | 10/2007 | Beatty et al. |
| 7,513,257 B2 | 4/2009 | Schulman et al. |
| 7,526,342 B2 | 4/2009 | Chin et al. |
| 7,603,159 B2 * | 10/2009 | Rasche ........................ 600/424 |
| 7,621,754 B2 | 11/2009 | Costello |
| 7,655,014 B2 * | 2/2010 | Ko et al. ....................... 606/129 |
| 7,684,858 B2 | 3/2010 | He et al. |
| 2002/0042594 A1 * | 4/2002 | Lum et al. .................... 604/117 |
| 2003/0199938 A1 | 10/2003 | Smits et al. |
| 2004/0034351 A1 | 2/2004 | Sherman et al. |
| 2004/0116878 A1 | 6/2004 | Byrd et al. |
| 2005/0113894 A1 | 5/2005 | Zilberman et al. |
| 2005/0119660 A1 * | 6/2005 | Bourlion et al. ................ 606/80 |
| 2005/0251237 A1 | 11/2005 | Kuzma et al. |
| 2006/0069436 A1 | 3/2006 | Sutton et al. |
| 2006/0111728 A1 | 5/2006 | Abdou |
| 2006/0149278 A1 | 7/2006 | Abdou |
| 2006/0149288 A1 | 7/2006 | Florentino |
| 2006/0189971 A1 | 8/2006 | Tasto et al. |
| 2006/0195102 A1 | 8/2006 | Malandain |
| 2006/0217705 A1 * | 9/2006 | Godara et al. .................. 606/41 |
| 2006/0293626 A1 | 12/2006 | Byrum et al. |
| 2007/0038052 A1 | 2/2007 | Swoyer et al. |
| 2007/0038078 A1 | 2/2007 | Osadchy |
| 2007/0078503 A1 | 4/2007 | Kuzma |
| 2007/0156012 A1 | 7/2007 | Tracey et al. |
| 2007/0249992 A1 | 10/2007 | Bardy |
| 2008/0033356 A1 * | 2/2008 | Kluge et al. .................. 604/117 |
| 2008/0269740 A1 | 10/2008 | Bonde et al. |
| 2009/0076521 A1 | 3/2009 | Hansen |
| 2009/0105743 A1 | 4/2009 | Chu |
| 2009/0182401 A1 | 7/2009 | Glukhovsky |
| 2009/0182402 A1 | 7/2009 | Glukhovsky |
| 2010/0036465 A1 | 2/2010 | Glukhovsky et al. |
| 2010/0174306 A1 | 7/2010 | Mitelberg et al. |
| 2010/0240240 A1 | 9/2010 | Ochoa et al. |

OTHER PUBLICATIONS

Salter et al., "First Clinical Experience with BION Implants for Therapeutic Electrical Stimulation," A.E. Mann Institute for Biomedical Engineering, ©1994 *International Neuromodulation Society*; 1094-7159, *Neuromodulation*, vol. 7, No. 1, 2004 38-47.

"SEXTANT™ Percutaneous Rod Insertion—Pedicle Screws," spineuniverse.com, [online] [Retrieved from the Internet on Feb. 21, 2005], Retrieved from the Internet URL[http://www.spineuniverse.com/displayarticle.php/article1575.html].

Non-Final Office Action for U.S. Appl. No. 11/972,393, mailed Dec. 15, 2010.

Non-Final Office Action for U.S. Appl. No. 11/972,396, mailed Dec. 14 2010.

Non-Final Office Action for U.S. Appl. No. 11/856,833, mailed Jan. 19, 2011.

* cited by examiner

METHODS AND APPARATUS FOR IMPLANTING ELECTRONIC IMPLANTS WITHIN THE BODY

CROSS-REFERENCE TO RELATED APPLICATIONS

This application is related to U.S. patent application Ser. Nos. 11/972,393 and 11/972,396, each entitled "Methods and Apparatus for Implanting Electronic Implants within the Body," filed on the same date, each of which is incorporated herein by reference in their entirety.

BACKGROUND

The invention relates generally to medical devices and procedures, and more particularly to apparatus and methods for implanting electronic implants within the body.

Electronic implants, such as, for example, electrical stimulation leads and/or electrical sensing leads, are used in various medical procedures. For example, some known electronic implants can be implanted within a patient's body to stimulate a response from a bodily organ or tissue, such as, for example, the heart, a muscle group or the like. Some known electronic implants can be implanted within a patient's body to sense a response from a bodily organ or tissue. Accordingly, known electronic implants can be inserted into the patient's body in a known location and/or orientation (e.g., such that a portion of the implant is in electrical contact with a nerve).

Known methods for implanting electronic implants within a patient's body can include first locating a desired target tissue using an targeting probe and then inserting the electronic implant adjacent the target tissue. Such known methods can include inserting the electronic implant via a passageway having a shallow angle relative to the skin surface (i.e., a passageway that is offset from the skin surface by a small angle). This method of insertion can be used, for example, to ensure that there is sufficient bodily tissue depth to maintain the position of the electronic implant when the target tissue is located at a shallow depth below the skin surface. Such known methods, however, often fail to accurately position the electronic implant adjacent the target tissue.

Thus, a need exists for improved methods and apparatus for implanting electronic implants within a patient's body.

SUMMARY

Apparatus and methods for implanting electronic implants within the body are described herein. In some embodiments, an apparatus includes an implant delivery device configured to deliver an implant into a body. The implant delivery device includes a target member, an insertion member and an electronic circuit system. The target member has a distal end portion configured to be disposed within the body adjacent a target location, which can be, for example, a nerve, a muscle or the like. The insertion member is movably coupled to the target member. A distal end portion of the insertion member is configured to be disposed within the body and selectively coupled to the implant. The electronic circuit system is configured to produce an electronic signal in proportion to a distance between the distal end portion of the target member and the distal end portion of the insertion member when the target member and the insertion member are disposed within the body. In some embodiments, the electronic signal is associated with an impedance between the distal end portion of the target member and the distal end portion of the insertion member. In other embodiments, the electronic signal is associated with any other suitable electronic characteristic, such as for example, a resistance between the distal end portion of the target member and the distal end portion of the insertion member, a capacitance between the distal end portion of the target member and the distal end portion of the insertion member, and/or an inductance between the distal end portion of the target member and the distal end portion of the insertion member.

DETAILED DESCRIPTION

Figure 1:
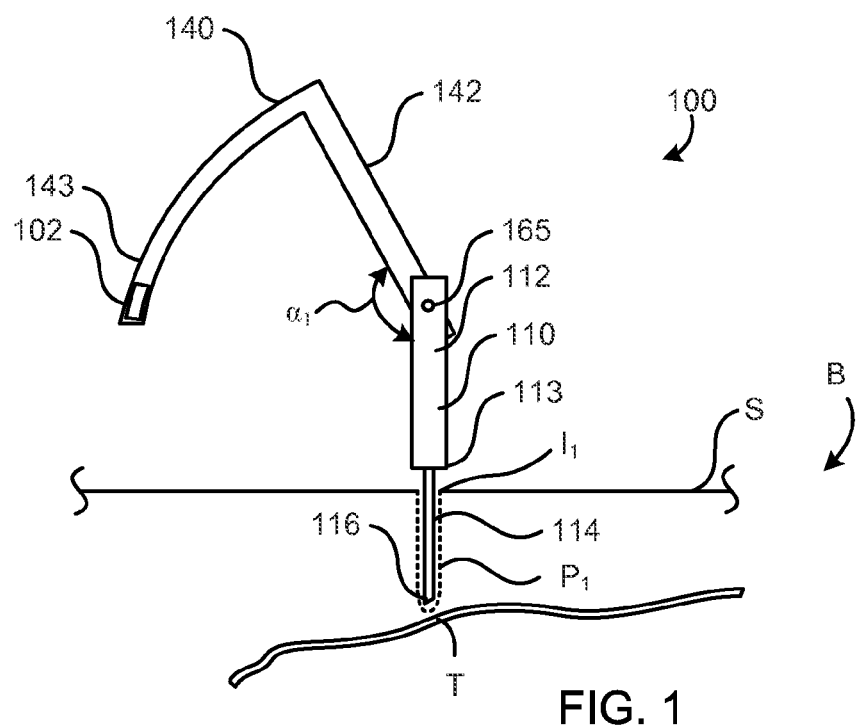
FIGS. 1-3 are schematic illustrations of a medical device according to an embodiment of the invention in a first configuration, a second configuration, and a third configuration, respectively.

In some embodiments, an apparatus includes a first member and a second member operatively coupled to the first member. The first member has a proximal end portion and a distal end portion. The distal end portion of the first member includes a target probe. The second member has a proximal end portion and a distal end portion. The distal end portion of the second member is configured to be selectively coupled to an electronic implant, such as, for example, a microstimulator, an elongate implant, an electronic lead, an electrode, and/or a sensor.

In some embodiments, an apparatus includes a first member and a second member movably coupled to the first member. The first member has a target portion configured to define a first passageway within a body. The first passageway extends from a first insertion location to a target location within the body. The second member is configured to define a second passageway within the body when the target portion of the first member is within the body. The second passageway, which is distinct from the first passageway, extends from a second insertion location to the target location.

In some embodiments, an apparatus includes a first member and a second member movably coupled to the first member. The first member has a target portion configured to define a first passageway within a body. The first passageway extends from a first insertion location to a target location within the body. The second member has a distal end portion and a proximal end portion. The distal end portion is configured to define a second passageway within the body when the target portion of the first member is within the body. The second passageway, which is distinct from the first passageway, extends from a second insertion location to the target location. The distal end portion is further configured to be selectively coupled to an electronic implant such that the second member can deliver the electronic implant from a location outside of the body to the target location within the body via the second passageway. The proximal end portion of the second member includes an actuator configured to selectively decouple the distal end portion of the second member from the electronic implant.

In some embodiments, an apparatus includes an implant delivery device configured to deliver an electronic implant into a body. The implant delivery device includes a target portion and an insertion portion, and has a first configuration and a second configuration. The target portion of the implant delivery device is configured to be disposed within the body and convey an electrical signal between a target location within the body and an electrical device disposed outside of the body when the implant delivery device is in the first configuration. A distal end portion of the insertion portion is configured to be disposed outside of the body when the implant delivery device is in the first configuration. The distal end portion of the insertion portion is configured to be disposed within the body at the target location when the implant delivery device is in the second configuration. In some embodiments, for example, the distal end portion of the insertion portion is configured to be selectively coupled to the electronic implant.

In some embodiments, an apparatus includes an elongate member and a target device. The elongate member is configured to be selectively coupled to an electronic implant, such as, for example, a microstimulator, an elongate implant, an electronic lead, an electrode, and/or a sensor. The target device includes a first portion and a second portion. The first portion of the target device defines a lumen configured to receive at least a portion of a target probe, which can, for example, electrically stimulate at least one of a nerve or a muscle when the target probe is within the body. The second portion of the target device defines a lumen configured to receive at least a portion of the elongate member. The second portion of the target device is configured to move relative to the first portion of the target device between a first position and a second position. A portion of a center line of the lumen of the first portion and a portion of a center line of the lumen of the second portion define a first angle when the second portion of the target device is in the first position. The portion of the center line of the lumen of the first portion and the portion of the center line of the lumen of the second portion define a second angle when the second portion of the target device is in the second position. The second angle is different than the first angle.

In some embodiments, a method includes inserting a target probe along a first path within a body such that a portion of the target probe is disposed adjacent a target location within the body. The target location can be, for example, a portion of a nerve, a muscle or the like. An electronic implant is inserted along a second path within the body such that a portion of the electronic implant is disposed adjacent the target location within the body. The second path is different from the first path. The electronic implant is inserted when the target probe is disposed adjacent the target location within the body.

In some embodiments, a method includes inserting a target probe of a first member of an implant delivery device into a body via a first incision such that a portion of the target probe is disposed within the body adjacent a target location. A second member of the implant delivery device is moved relative to the first member such that a distal end portion of the second member is moved from a region outside of the body to the target location within the body via a second incision. The second incision is physically distinct from the first incision. The distal end portion of the second member is selectively coupled to an electronic implant. In some embodiments, the method further includes decoupling the electronic implant from the distal end portion of the second member after the second member of the implant delivery device is moved.

In some embodiments, a method includes engaging a target device with an outer surface of a body. The target device includes a first portion and a second portion. The first portion defines a lumen and the second portion defines a lumen. A distal end portion of a target probe is inserted into the body via the lumen of the first portion. The second portion of the target device is moved relative to the first portion of the target device. In some embodiments, for example, the second portion of the target device can be rotated within an opening defined by the first portion of the target device. A distal end portion of an implant delivery member is inserted into the body via the lumen of the second portion. In some embodiments, for example, the distal end portion of the implant delivery member is selectively coupled to an electronic implant and the method can further include decoupling the distal end portion of the implant delivery member and the electronic implant.

In some embodiments, an apparatus includes an implant delivery device configured to deliver an implant into a body. The implant delivery device includes a target member, an insertion member and an electronic circuit system. The target member has a distal end portion configured to be disposed within the body adjacent a target location, which can be, for example, a nerve, a muscle or the like. The insertion member is movably coupled to the target member. A distal end portion of the insertion member is configured to be disposed within the body and selectively coupled to the implant. The electronic circuit system is configured to produce an electronic signal in proportion to a distance between the distal end portion of the target member and the distal end portion of the insertion member when the target member and the insertion member are disposed within the body. In some embodiments, the electronic signal is associated with an impedance between the distal end portion of the target member and the distal end portion of the insertion member. In other embodiments, the electronic signal is associated with any other suitable electronic characteristic, such as for example, a resistance between the distal end portion of the target member and the distal end portion of the insertion member, a capacitance between the distal end portion of the target member and the distal end portion of the insertion member, and/or an inductance between the distal end portion of the target member and the distal end portion of the insertion member.

In some embodiments, an apparatus includes an implant delivery device configured to deliver an implant into a body. The implant delivery device includes a target member, an insertion member and position indicator. The target member has a distal end portion configured to be disposed within the body adjacent a target location. The insertion member is movably coupled to the target member. A distal end portion of the insertion member is configured to be disposed within the body and selectively coupled to the implant. The position indicator is configured to indicate a position of the distal end portion of the target member relative to the distal end portion of the insertion member when the target member and the insertion member are disposed within the body. In some embodiments, for example, the position indicator includes a first portion and a second portion. The first portion is coupled to the target member and includes a plurality of graduated markings. The second portion is coupled to the insertion member and includes a pointer configured to move relative to the graduated markings of the first member.

In some embodiments, a method includes inserting a distal end portion of a target probe into a body. An implant is inserted into the body. A distance between the distal end portion of the target probe and the implant is measured after the distal end portion of the target probe is inserted and the implant is inserted. The implant is moved within the body in response to the measuring.

In some embodiments, a method includes inserting a distal end portion of a target probe into a body using an implant delivery device via a first incision. An implant is inserted into the body using the implant delivery device via a second incision. The second incision is physically distinct from the first incision. A distance between the distal end portion of the target probe and the implant is measured after the distal end portion of the target probe is inserted and the implant is inserted. The implant is moved within the body in response to the measuring.

As used in this specification, the words "proximal" and "distal" refer to the direction closer to and away from, respectively, an operator (e.g., surgeon, physician, nurse, technician, etc.) who would use a medical device or a therapeutic device during a procedure. For example, the end of a medical device first to contact and/or be inserted into the patient's body would be the distal end, while the opposite end of the medical device (e.g., the end of the medical device being operated by the operator or the end of the medical device last to be inserted into the patient's body) would be the proximal end of the medical device.

The term "parallel" is used herein to describe a relationship between two objects (e.g., a first tubular member, a second tubular member, a lumen or the like) and/or the geometric constructions defined by two objects (e.g., a longitudinal axis) in which the two objects and/or the two geometric constructions are substantially non-intersecting if they extend substantially to infinity. For example, as used herein in the context of geometrical constructions, when a planar surface (i.e., a two-dimensional surface) is said to be parallel to a line (e.g., a longitudinal axis), every point along the line is spaced apart from the nearest portion of the planar surface by a substantially equal distance. Similarly, as used herein in the context of two objects, a first object (e.g., a first tubular member) is said to be parallel to a second object (e.g., a second tubular member) when a longitudinal axis of the first object and a longitudinal axis of the second object do not intersect if they were extended to infinity. Two objects and/or geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The term "normal" is used herein to describe a relationship between two objects (e.g., a first tubular member, a second tubular member, a lumen or the like) and/or the geometric constructions defined by two objects (e.g., a longitudinal axis, a planar surface or the like) in which the two objects and/or the two geometric constructions intersect at an angle of approximately 90 degrees within at least one plane. For example, as used herein in the context of two objects, a first object is said to be normal to a second object when a longitudinal axis of the first object and a longitudinal axis of the second object intersect at an angle of approximately 90 degrees within a plane.

The terms "member" and "device" as used herein can refer to either a single item or multiple items that cooperatively perform one or more functions. For example, as used herein, a member can include a single component or can be constructed from multiple components coupled together. More particularly, when a member includes a single component, the single component can be, but is not necessarily, monolithically constructed from a single material. When a member is constructed from multiple components, in some embodiments, the various components can move relative to each other. Conversely, in other embodiments, the various components from which the member is constructed can be in a fixed position relative to each other whether or not monolithically formed.

The term "electronic implant" as used herein can refer to either an implant including active electronic circuitry or an implant including a passive portion of an electronic circuit system. For example, as used herein, an electronic implant can include active devices, such as microstimulators, amplifiers, power supplies, sensors or the like. An electronic implant can also include passive devices, such as passive leads, wires, or the like.

Figure 2:
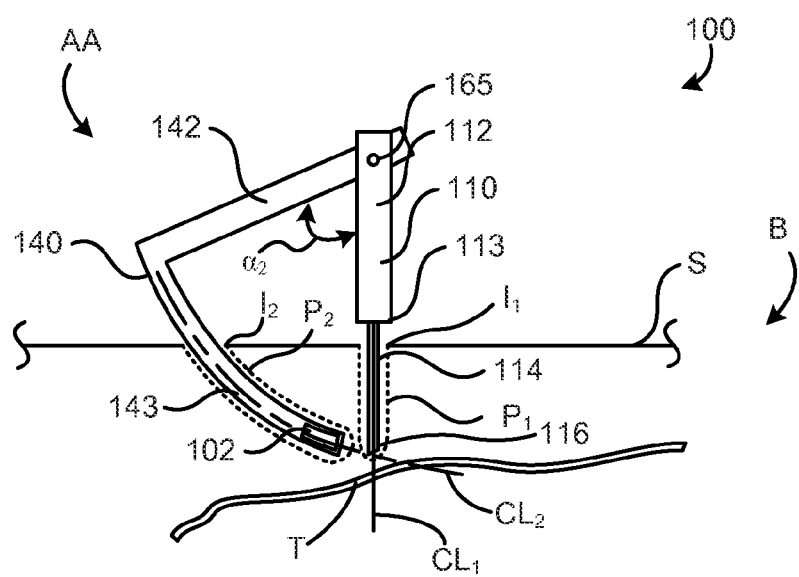
Figure 3:
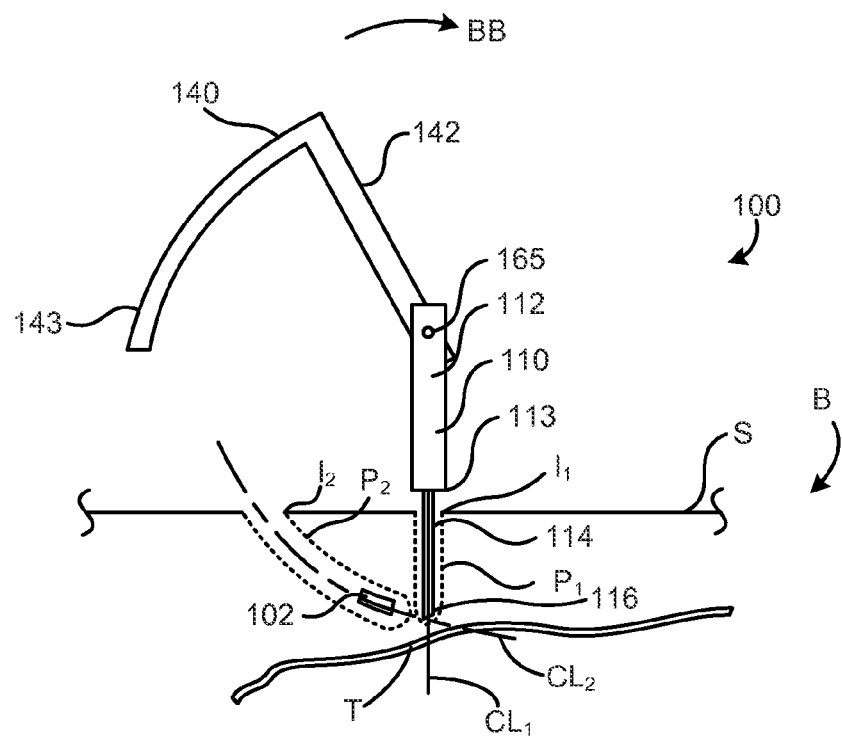

FIGS. 1-3 are schematic illustrations of a medical device 100 according to an embodiment of the invention in a first configuration, a second configuration, and a third configuration, respectively. The medical device 100 includes a target member 110 and an insertion member 140. The target member 110 has a proximal end portion 112 and a distal end portion 113. The distal end portion 113 includes a target probe 114 configured to locate a target tissue T within the body B. For example, in some embodiments, the target probe 114 can be an electronic stimulating probe having an exposed electrode configured to stimulate a muscle, a nerve or the like and/or receive an electronic signal from a muscle, nerve or the like to locate the target tissue T.

The insertion member 140 has a proximal end portion 142 and a distal end portion 143. The distal end portion 143 of the insertion member 140 is selectively coupled to an implant 102. The selective coupling of the distal end portion 143 of the insertion member 140 and the implant 102 can be accomplished by any suitable means, such as, for example, a mechanical coupling (e.g., an interference fit, detents, a threaded coupling, or the like), an electronic coupling (e.g., a magnetic coupling), a chemical bond, a hydraulic coupling and/or a pneumatic coupling (e.g., a vacuum coupling). The implant 102 can be an electronic implant, such as, for example, a microstimulator, an elongate implant, an electronic lead, an electrode, a power supply, an amplifier and/or a sensor. Although the implant 102 is shown as being coupled to the distal-most portion of the insertion member 140, in other embodiments, the implant 102 can be selectively coupled in any suitable location along the distal end portion 143 of the insertion member 140.

The proximal end portion 142 of the insertion member 140 is rotatably coupled to the proximal end portion 112 of the target member 110 at a coupling joint 165. The coupling joint 165 can include, for example a pin, a ball and socket joint, a hinge or the like. In this manner, the insertion member 140 can rotate relative to the target member 110 about the coupling joint 165. Said another way, the proximal end portion 142 of the insertion member 140 can rotate about an axis substantially normal to a longitudinal axis of the target member 110. Moreover, in some embodiments, such as, for example, those embodiments in which the coupling joint 165 is a ball and socket joint, the proximal end portion 142 of the insertion member 140 can rotate about the longitudinal axis of the target member 110. In this manner, as described in more detail herein, the proximal end portion 142 of the insertion member 140 can be rotated to allow for multiple locations of the insertion 12.

As shown in FIG. 1, the medical device 100 can be placed in the first configuration by inserting the distal end portion 113 of the target member 110 into the body B through a first incision $I_1$ in the skin S. The distal end portion 113 is inserted via a first passageway $P_1$ such that the distal tip 116 of the target probe 114 is adjacent the target tissue T. In some embodiments, the distal tip 116 of the target probe 114 is configured to pierce, dilate and/or displace bodily tissue to define the first passageway $P_1$ to locate the target tissue T. Said another way, when the medical device 100 is in the first configuration, the distal tip 116 of the target probe 114 is positioned at a predetermined location (e.g., proximate a particular anatomical structure, at a desired depth or the like) within the patient's body B. Although the distal tip 116 of the target probe 114 is shown as being adjacent the target tissue T, in other embodiments, the target member 110 can be inserted such that the distal tip 116 of the target probe 114 is within the body B at a depth greater than a depth of the target tissue T. Said another way, in some embodiments, the target member 110 can be inserted such that the a portion of the target probe 114 other than the distal tip 116 is adjacent the target tissue T.

When the medical device 100 is in the first configuration, the distal end portion 143 of the insertion member 140 is coupled to the implant 102. Additionally, the insertion member 140 is in a first position relative to the target member 110 such that the distal end portion 143 of the insertion member 140 is disposed outside of the body B. Similarly stated, when the medical device 100 is in the first configuration, the insertion member 140 is angularly offset from the target member 110 by a first angle $\alpha_1$. In some embodiments, the medical device 100 can be maintained in its first configuration by a ratchet mechanism, a detent, a biasing member, a locking mechanism or the like.

When the distal tip 116 of the target probe 114 is adjacent the target tissue T, the insertion member 140 can be rotated relative to the target member 110 as shown by the arrow AA in FIG. 2. In this manner, the medical device 100 can be moved between the first configuration and the second configuration. When the medical device 100 is in the second configuration, the insertion member 140 is in a second position relative to the target member 110 such that the distal end portion 143 of the insertion member 140 is disposed within the body B. Similarly stated, when the medical device 100 is in the second configuration, the insertion member 140 is angularly offset from the target member 110 by a second angle $\alpha_2$. In some embodiments, the medical device 100 can be maintained in its second configuration by a ratchet mechanism, a detent, a biasing member, a locking mechanism or the like. Similarly, in some embodiments, the movement of the insertion member 140 relative to the target member 110 can be limited by a mechanical stop, a detent, a locking mechanism, a ratchet mechanism or the like. In this manner, the movement of the insertion member 140 relative to the target member 110 can be controlled to prevent the distal end portion 143 of the insertion member 140 from overshooting (i.e., moving past) the target tissue T and/or the distal tip 116 of the target probe 114.

When the medical device 100 is moved between the first configuration (FIG. 1) and the second configuration (FIG. 2), the distal end portion 143 of the insertion member 140 is inserted into the body B through a second incision $I_2$ in the skin S. The distal end portion 143 of the insertion member 140 is moved within the body B via a second passageway $P_2$ such that the distal end portion 143 of the insertion member 140 is adjacent the target tissue T and/or the distal tip 116 of the target probe 114. Said another way, when the medical device 100 is moved between the first configuration and the second configuration, the insertion member 140 is moved relative to the target member 110 between the first position and the second position such that the distal end portion 143 of the insertion member 140 is moved from a region outside of the body to a region within the body B. Moreover, when the medical device 100 is moved between the first configuration and the second configuration, the distal end portion 143 of the insertion member 140 remains coupled to the implant 102. Accordingly, when the medical device 100 is moved between the first configuration and the second configuration, the implant 102 is moved from a region outside of the body to a region within the body B.

In some embodiments, the distal end portion 143 of the insertion member 140 is configured to pierce, dilate and/or displace bodily tissue to define the second passageway $P_2$. For example, in some embodiments, the distal end portion 143 of the insertion member 140 can include a tapered tip (not shown in FIGS. 1-3). In other embodiments, a distal portion of the implant 102 can extend from the distal end portion 143 of the insertion member and be configured to pierce, dilate and/or displace bodily tissue to define the second passageway $P_2$.

As shown in FIG. 2, the first passageway $P_1$ extends along a substantially linear path from the first incision $I_1$ to a region within the body B adjacent the target tissue T. Although the first passageway $P_1$ is shown as being substantially linear, in other embodiments, the first passageway $P_1$ can be of any suitable shape. Similarly, the second passageway $P_2$ extends along a curved path from the second incision $I_2$ to a region within the body B adjacent the target tissue T. Although the second passageway $P_2$ is shown as being curved, in other embodiments, the second passageway $P_2$ can be of any suitable shape. Moreover, the second incision $I_2$ is physically distinct from the first incision $I_1$. Said another way, the first incision $I_1$ and the second incision $I_2$ do not share a common boundary. In this manner, the size of the first incision $I_1$ and/or the second incision $I_2$ can be minimized to reduce patient trauma.

Similarly, the first passageway $P_1$ is distinct from the second passageway $P_2$. Said another way, at least a portion of the first passageway $P_1$ and at least a portion of the second passageway $P_2$ do not share a common border. Moreover, as shown in FIG. 2, a center line $CL_1$ of the first passageway $P_1$ and a center line $CL_2$ of the second passageway $P_2$ are angularly offset. In some embodiments, for example, a portion of the center line $CL_2$ of the second passageway $P_2$ can be substantially normal to a portion of the center line $CL_1$ of the first passageway $P_1$ and/or the targeting probe 114.

When the distal end portion 143 of the insertion member 140 and/or the implant 102 is adjacent the target tissue T, the distal end portion 143 of the insertion member 140 can be decoupled from the implant 102. The insertion member 140 can then be rotated relative to the target member 110 as shown by the arrow BB in FIG. 3, thereby placing the medical device 100 in the third configuration. When the medical device 100 is moved between the second configuration (FIG. 2) and the third configuration (FIG. 3), the distal end portion 143 of the insertion member 140 is removed from within the body B via the second passageway P2 and the second incision $I_2$. Said another way, when the medical device 100 is moved between the second configuration and the third configuration, the insertion member 140 is moved relative to the target member 110 between the second position and a third position such that the distal end portion 143 of the insertion member 140 is moved from a region within the body B to a region outside of the body, while the implant 102 remains within the body B adjacent the target tissue T and/or the distal tip 116 of the target probe 114.

FIGS. 4-7 are front views of a medical device 200 according to an embodiment of the invention in a first configuration, a second configuration, a third configuration, and a fourth configuration, respectively. The medical device 200 includes a target member 210, an insertion member 240, and a coupling member 264. The target member 210 has a proximal end portion 212 and a distal end portion 213. The distal end portion 213 includes an anchor portion 228 having a contact surface 220 configured to be disposed against the skin S of a body B. In this manner, the position of the target member 210 relative to the body B can be maintained throughout the operation of the medical device 200. In some embodiments, for example, the anchor portion 228 and/or the contact surface 220 can be configured to limit movement of the target member 210 relative to the body B when the contact surface 220 against the skin S. For example, in some embodiments, the contact surface 220 can include a layer of adhesive (not shown in FIGS. 4-7). In other embodiments, the anchor portion 228 can include straps, fasteners and/or any other suitable mechanism for limiting movement of the target member 210 relative to the body B (not shown in FIGS. 4-7).

A target probe 214 is movably coupled to the target member 210. In some embodiments, for example, the target probe 214 can be slidably disposed within a lumen (not shown in FIGS. 4-7) defined by target member 210. In other embodiments, the target probe 214 can be slidably disposed against an outer surface of the target member 210. The target probe 214 has a proximal end portion 215 and a distal end portion 216 (see e.g., FIG. 6). The proximal end portion 215 includes multiple graduated markings 218 that indicate the position of the target probe 214 relative to the target member 210. Similarly stated, the graduated markings 218 of the proximal end portion 215 can indicate the distance between the distal end portion 216 of the target probe 214 and the distal end portion 213 of the target member 210. In this manner, as shown in FIG. 5, the graduated markings 218 can indicate the depth D of the insertion of the target probe 214.

The insertion member 240 has a proximal end portion 242 and a distal end portion 243. As shown in FIG. 5, the insertion member 240 is curved such that at least a portion of the insertion member 240 is characterized by a radius of curvature R. As described in more detail below, the curved shape of the insertion member 240 contributes to the trajectory of the passageway formed by the insertion member 240 when the insertion member 240 is inserted into the body B. In some embodiments, the center point of the radius of curvature R is coincident with the coupling joint 265. In other embodiments, however, the center point of the radius of curvature R can be offset from the coupling joint 265. Similarly, in some embodiments the radius of curvature R can be substantially the same as the length $L_2$ of the coupling member 264. In other embodiments, however, the radius of curvature R can be different from the length $L_2$ of the coupling member 264.

Figure 7:
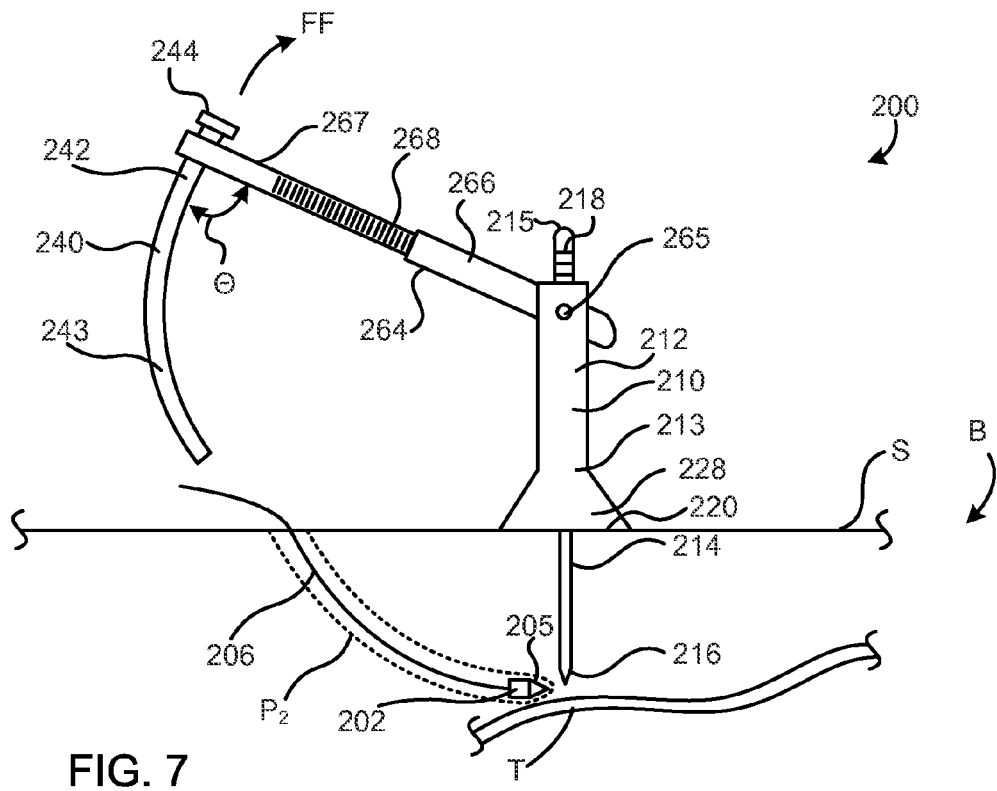

The distal end portion 243 of the insertion member 240 is selectively coupled to an implant 202. The selective coupling of the distal end portion 243 of the insertion member 240 and the implant 202 can be accomplished by any suitable means, as described above. The implant 202 includes a distal end 205 configured to extend from distal end portion 243 of the insertion member 240. The distal end portion 205 of the implant 202 is tapered such that the distal end portion 205 can pierce, dilate and/or displace bodily tissue. As shown in FIG. 7, a lead wire 206 is coupled to the proximal end portion of the implant 202. As described above, the implant 202 can be an electronic implant, such as, for example, a microstimulator, an elongate implant, an electronic lead, an electrode, a power supply, an amplifier and/or a sensor.

The proximal end portion 242 of the insertion member 240 includes an actuator 244 configured to selectively couple and/or decouple the distal end portion 243 of the insertion member 240 from the implant 202. In this manner, as described in more detail herein, when the implant 202 is disposed within the body B adjacent the target tissue T, a user can actuate the actuator 244 to decouple the distal end portion 243 of the insertion member 240 from the implant 202. Similarly, the user can actuate the actuator 244 to couple the distal end portion 243 of the insertion member to the implant 202 to facilitate removal of the implant 202 from the body B and/or repositioning the implant 202 within the body B. The actuator 244 can be any suitable actuator, such as for example, a mechanical actuator, an electrical actuator, a hydraulic actuator, a pneumatic actuator or the like.

The insertion member 240 is rotatably coupled to the target member 210 by the coupling member 264, which includes a first end portion 266 and a second end portion 267. The first end portion 266 of the coupling member 264 is rotatably coupled to the proximal end portion 212 of the target member 210 at the coupling joint 265. In this manner, the coupling member 264, and therefore the insertion member 240, can rotate relative to the target member 210 about the coupling joint 265. Said another way, the coupling member 264 can rotate relative to the target member 210 to change the angle α between the coupling member 264 and the target member 210. Similarly, the second end portion 267 of the coupling member 264 is rotatably coupled to the proximal end portion 242 of the insertion member 240. In this manner, the insertion member 240 can rotate relative to the target member 210 independent from the rotation of the coupling member 264 relative to the target member 210. Said another way, the insertion member 240 can rotate relative to the coupling member 264 to change the angle Θ between the insertion member 240 and the coupling member 264.

As shown in FIG. 5, the second end portion 267 of the coupling member 264 includes multiple graduated markings 268 and is movably coupled to the first end portion 266 of the coupling member 264. In this manner, the length $L_2$ of the coupling member 264 can be changed during the operation of the medical device 200. Although the second end portion 267 of the coupling member 264 is shown as being slidably disposed within a portion of the first end portion 266 of the coupling member, in other embodiments, the second end portion 267 and the first end portion 266 can be movably coupled together in any suitable arrangement.

Figure 4:
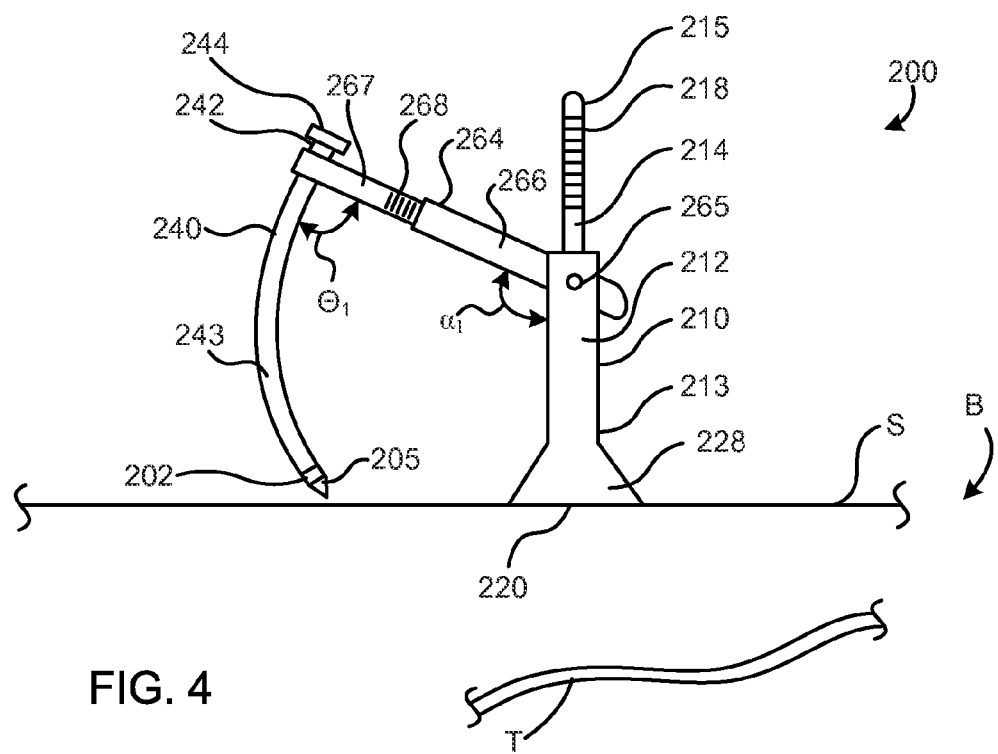
FIGS. 4-7 are front views of a medical device according to an embodiment of the invention in a first configuration, a second configuration, a third configuration, and a fourth configuration, respectively.
Figure 5:
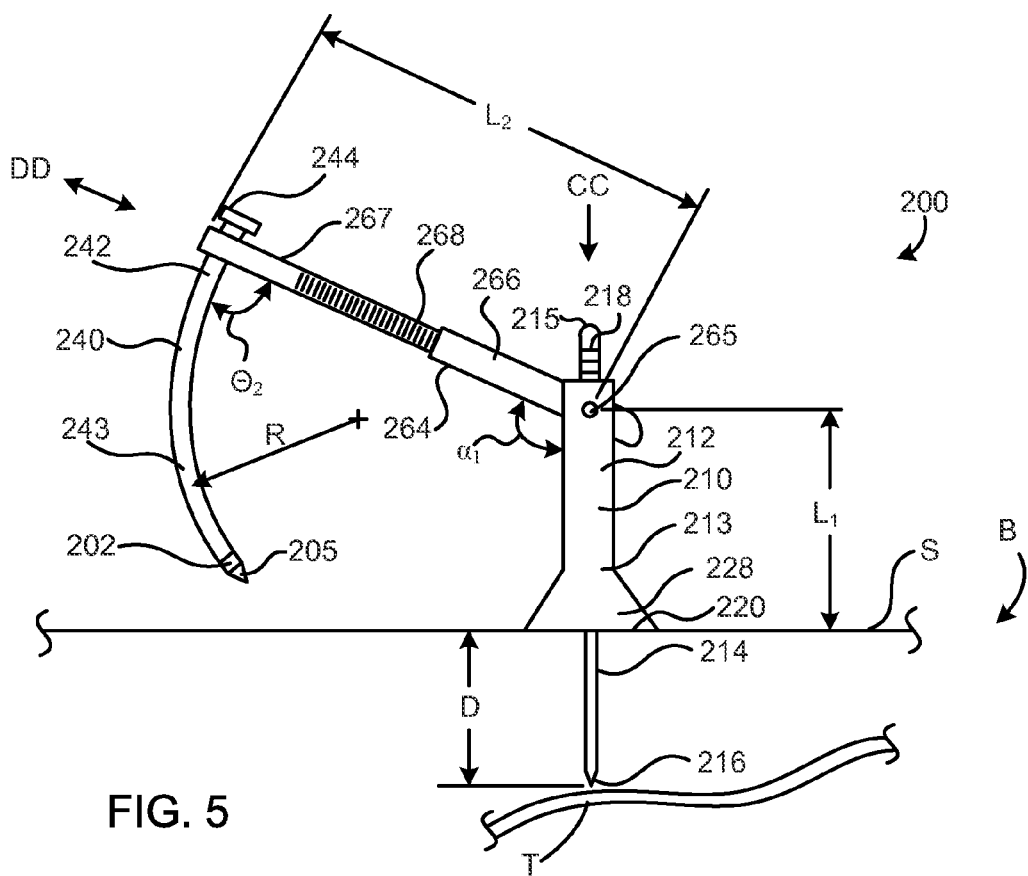

As shown in FIG. 4, the medical device 200 can be placed in the first configuration by disposing the distal end portion 213 of the target member 210 against the body B. When the medical device 200 is in the first configuration, the contact surface 220 can engage the skin S to maintain a position of the target portion 210 relative to the skin S. In this manner, after the user determines the appropriate position on the body B for insertion of the target probe 214, the target member 210 can be securely positioned against the body B.

When the medical device 200 is in the first configuration, the distal end portion 243 of the insertion member 240 is coupled to the implant 202. Additionally, the insertion member 240 is in a first position relative to the target member 210 and/or the coupling member 264 such that the distal end portion 243 of the insertion member 240 is disposed outside of the body B. Similarly stated, when the medical device 200 is in the first configuration, the coupling member 264 is angularly offset from the target member 210 by a first angle $\alpha_1$ and the insertion member 240 is angularly offset from the coupling member 264 by a first angle $\Theta_1$. In some embodiments, the medical device 200 can be maintained in its first configuration by a ratchet mechanism, a detent, a biasing member, a locking mechanism and/or the like.

As shown in FIG. 5, the medical device 200 can be placed in the second configuration by inserting the distal end portion 216 of the target probe 214 into the body B, by changing the length $L_2$ of the coupling member 264, and/or by rotating the insertion member 240 relative to the coupling member 264. The distal end portion 216 of the target probe 214 is inserted by moving the target probe 214 relative to the target member 210, as shown by arrow CC. In this manner, the insertion of the target probe 214 is guided by the target member 210. The target probe 214 is moved relative to the target member 210 such that the distal end portion 216 of the target probe 214 is inserted through and/or defines a first incision (not identified in FIG. 5) in the skin S. As described above, the target probe 214 is moved within the body B along a first passageway (not identified in FIG. 5) such that the distal end portion 216 of the target probe 214 is adjacent the target tissue T. Similarly stated, the distal end portion 216 of the target probe 214 is inserted along and/or defines a first passageway to a predetermined depth D within the body B. As described above, the magnitude of the depth D can be indicated by the graduated markings 218 of the proximal end portion 215 of the target probe 214.

The length $L_2$ of the coupling member 264 can be changed by moving the second end portion 267 relative to the first end portion 266, as shown by arrow DD in FIG. 5. The length $L_2$ of the coupling member 264 can be indicated using the graduated markings 268. In some embodiments, the coupling member 264 can be maintained at a predetermined length $L_2$ by a detent, a biasing member, a locking mechanism and/or the like. Similarly, the insertion member 240 can be rotated relative to the coupling member 264 such that the insertion member 240 is angularly offset from the coupling member 264 by an angle $\Theta_2$ that is different from the angle $\Theta_1$. The orientation of the insertion member 240 relative to the coupling member 264 can be maintained by a detent, a biasing member, a locking mechanism and/or the like. By adjusting the length $L_2$ of the coupling member 264 and/or the angle between the insertion member 240 and the coupling member 264, the user can define a predetermined location for the incision and/or a predetermined trajectory of the passageway $P_2$ through which the distal end portion 243 of the insertion member 240 will be inserted into the body B.

In some embodiments, locating the target tissue T with the target probe 214 can be an iterative process. Accordingly, in some embodiments, the distal end portion 216 can be inserted into the body before the distal end portion 213 of the targeting member 210 is disposed against the body B. In this manner, the target tissue T can be located before the contact surface 220 is placed against and/or anchored to the skin S. In such embodiments, after the distal end portion 216 of the target tissue 214 is disposed adjacent the target tissue T, the target member 210 is moved about the target probe 214 until the contact surface 220 is disposed against the skin S.

Figure 6:
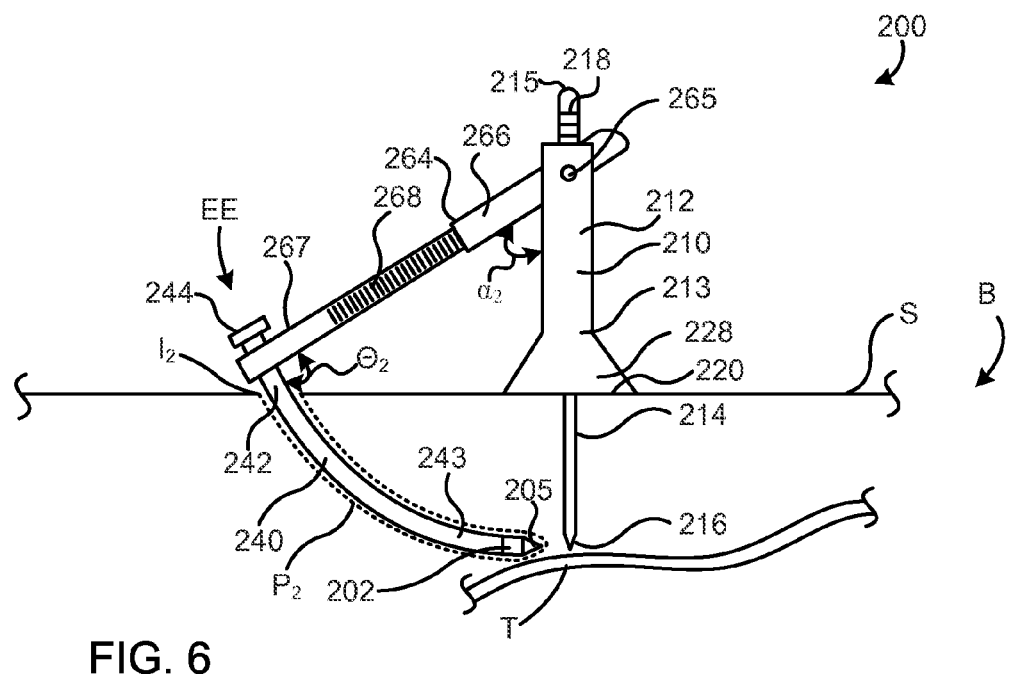

When the distal end portion 216 of the target probe 214 is adjacent the target tissue T and the length $L_2$ of the coupling member 264 and/or the angle $\Theta$ between the insertion member 240 and the coupling member 264 are adjusted, the insertion member 240 can be rotated relative to the target member 210 as shown by the arrow EE in FIG. 6. In this manner, the medical device 200 can be moved between the second configuration and the third configuration. When the medical device 200 is in the third configuration, the insertion member 240 is in a second position relative to the target member 210 such that the distal end portion 243 of the insertion member 240 is disposed within the body B. Similarly stated, when the medical device 200 is in the second configuration, the insertion member 240 is angularly offset from the target member 210 by a second angle $\alpha_2$.

When the medical device 200 is moved between the second configuration (FIG. 5) and the third configuration (FIG. 6), the distal end portion 243 of the insertion member 240 is inserted into the body B through a second incision $I_2$ in the skin S. The distal end portion 243 of the insertion member 240 is moved within the body B via a second passageway $P_2$ such that the distal end portion 243 of the insertion member 240 is adjacent the target tissue T and/or the distal end portion 216 of the target probe 214. When the medical device 200 is moved between the second configuration and the third configuration, the distal end portion 243 of the insertion member 240 remains coupled to the implant 202. Accordingly, when the medical device 200 is moved between the second configuration and the third configuration, the implant 202 is moved from a region outside of the body to a region within the body B.

As described above, the length $L_2$ of the coupling member 264 and/or the angle $\Theta$ between the insertion member 240 and the coupling member 264 can be adjusted based on the depth D of the target probe 214. In this manner, the second incision $I_2$ through which the distal end portion 243 of the insertion member 240 is disposed and/or the trajectory of the second passageway $P_2$ through which the distal end portion 243 of the insertion member 240 travels within the body B can be adjusted as desired. Similarly stated, the kinematic relationship between the target member 210, the coupling member 264 and/or the insertion member 240 allows the distal end portion 243 of the insertion member 240 to be inserted into the body B along multiple different passageways, each of which can terminate at the target tissue T. For example, in some embodiments, the medical device 200 can be adjusted to result in a large spacing between the first incision (not identified in FIGS. 4-7) and the second incision $I_2$ and a passageway having a shallow angle of entry into the body B. In other embodiments, however, the medical device 200 can be adjusted to result in a small spacing between the first incision and the second incision $I_2$ and a passageway having a steeper angle of entry into the body B.

When the distal end portion 243 of the insertion member 240 and/or the implant 202 is adjacent the target tissue T, the distal end portion 243 of the insertion member 240 can be decoupled from the implant 202 using the actuator 244. The insertion member 240 can then be rotated relative to the target member 210 as shown by the arrow FF in FIG. 7, thereby placing the medical device 200 in the fourth configuration. When the medical device 200 is moved between the third configuration (FIG. 6) and the fourth configuration (FIG. 7), the distal end portion 243 of the insertion member 240 is removed from within the body B via the second passageway P₂ and the second incision I₂, while the implant 202 remains within the body B. The lead wire 206 can extend from the body B through the second passageway P₂.

The distal end portion 243 of the insertion member 240 can be coupled to the implant 202 in any suitable manner that allows the selective coupling and/or decoupling of the distal end portion 243 and the implant 202, both within the body B and outside of the body B. For example, in some embodiments, the distal end portion 243 of the insertion member 240 can define a lumen configured to receive the implant 202. In this manner, the side wall insertion member 240 can prevent the implant 202 from contacting portions of the patient's body B during insertion. Said another way, when the medical device 200 is moved from the second configuration to the third configuration, the insertion member 240 can prevent the implant 202 from being damaged during insertion.

The target probe 214 can include any suitable target probe for locating the target tissue T within the body B. For example, in some embodiments, the target probe 214 can be a needle, a guide wire or the like configured to locate the target tissue T by mechanically stimulating a bodily tissue. In other embodiments, the target probe 214 can be a radio-opaque targeting probe configured to locate the target tissue T in conjunction with an imaging system. In yet other embodiments, the targeting probe 214 can include an electrode configured to convey an electrical signal between the target tissue T and an electrical device (not shown in FIGS. 4-7) disposed outside of the body B. For example, in some embodiments, the target probe 214 can be an electromyogram (EMG) needle configured to be percutaneously inserted into the body B to electrically stimulate and/or receive an electronic signal from the target tissue T. In some embodiments, the target probe 214 can be an EMG needle having a length of 25 mm to 75 mm and a diameter of 25 gage to 28 gage. In other embodiments, the target probe 214 can be an EMG needle having a diameter of 0.9 mm and length of 20-25 cm.

Figure 8:
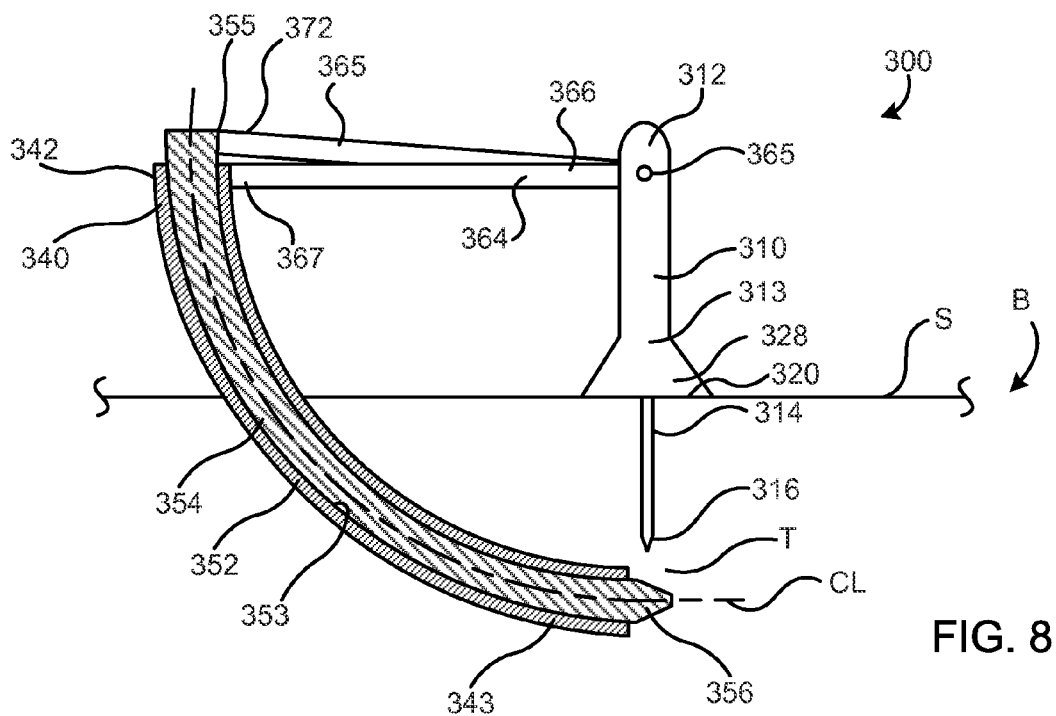
FIGS. 8-10 are partial cross-sectional front views of a medical device according to an embodiment of the invention in a first configuration, a second configuration, and a third configuration, respectively.
Figure 9:
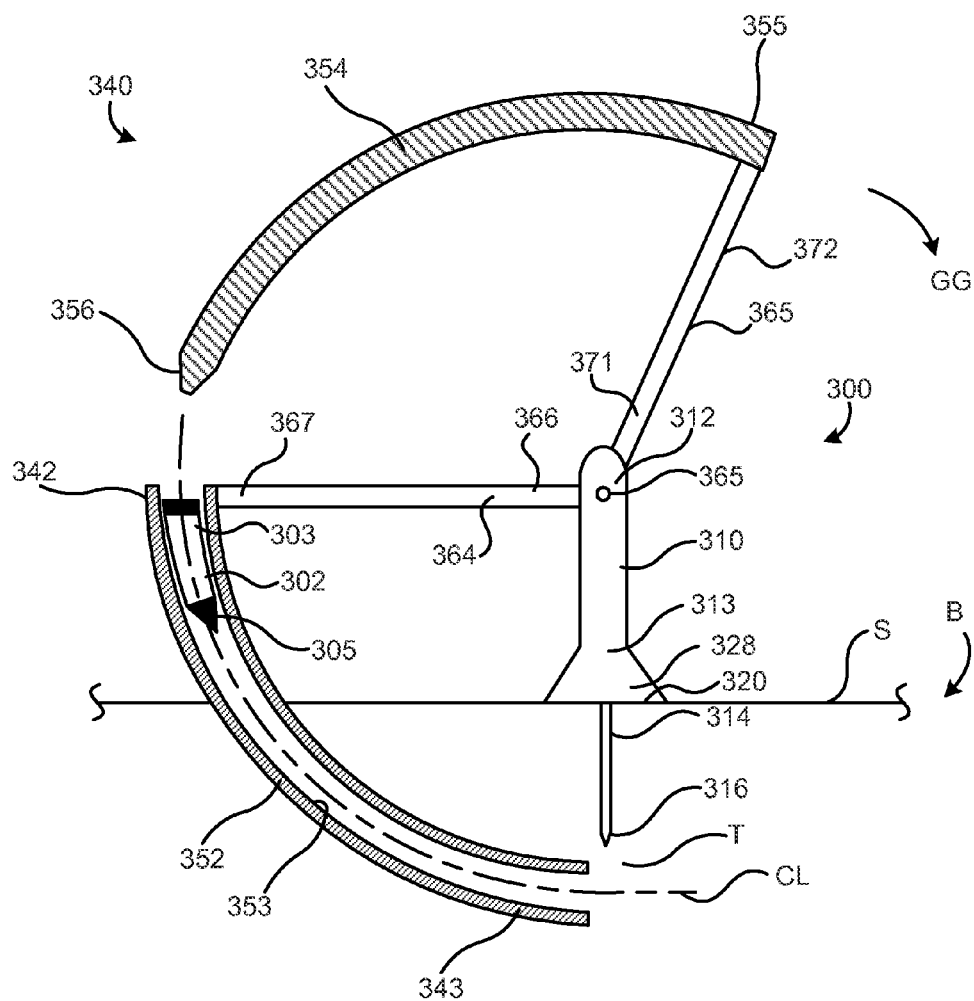
Figure 10:
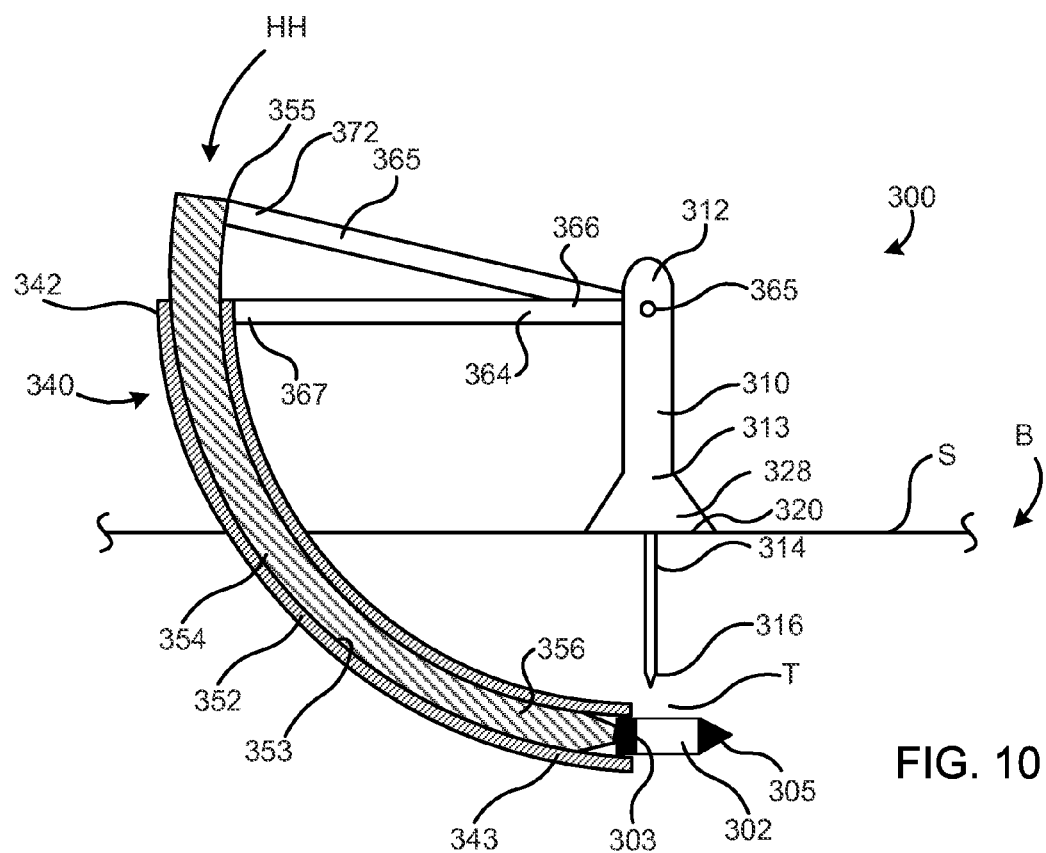

Although the insertion member 240 of the medical device 200 is shown as including a single structure configured to pierce the skin S, define the second passageway P2, and/or convey the implant 202 to the target tissue T, in other embodiments, an insertion member can include multiple components to perform the various functions described herein. For example, FIGS. 8-10 are partial cross-sectional side views of an implant insertion device 300 according to an embodiment of the invention. The implant insertion device 300 includes a target member 310, an insertion member 340, a first coupling member 364, and a second coupling member 365.

The target member 310 has a proximal end portion 312 and a distal end portion 313. The distal end portion 313 includes a target probe 314 configured to locate a target tissue T within the body B. For example, as described above, in some embodiments, the target probe 314 can be an electronic stimulating probe having an exposed electrode configured to stimulate and/or receive an electronic signal from a muscle, nerve or the like to locate the target tissue T. The distal end portion 313 of the target member 310 also includes an anchor portion 328 having a contact surface 320 configured to be disposed against the skin S of a body B when the distal tip 316 of the target probe 314 is adjacent the target tissue T. In this manner, the position of the target member 310 relative to the body B can be maintained throughout the operation of the implant insertion device 300.

The insertion member 340 includes a sheath 352 and a dilator 354, each of which are independently and movably coupled to the target member 310, as described in more detail below. The sheath 352 includes a proximal end portion 342 and a distal end portion 343 and defines a lumen 353 therethrough. The sheath 352 has a curved shape, which can characterize the trajectory of the insertion passageway formed in the body, as described above. The sheath 352 is rotatably coupled to the target member 310 by the first coupling member 364, which includes a first end portion 366 and a second end portion 367. The first end portion 366 of the first coupling member 364 is rotatably coupled to the proximal end portion 312 of the target member 310 via any suitable coupling joint at location 365. The second end portion 367 of the first coupling member 364 is coupled to the proximal end portion 342 of the sheath 352.

The dilator 354 includes a proximal end portion 355 and a distal end portion 356. The distal end portion 356 of the dilator 354 is tapered such that the distal end portion 356 can pierce, dilate and/or displace bodily tissue. Said another way, the distal end portion 356 of the dilator 354 is configured to define an incision and/or a passageway within the body B through which an implant can be inserted. As shown in FIGS. 8 and 10, at least a portion of the dilator 354 is configured to be disposed within the lumen 353 of the sheath 352. Similarly stated, the dilator 354 has a curved shape that corresponds to the curved shape of the sheath 352.

The dilator 354 is rotatably coupled to the target member 310 by the second coupling member 365, which includes a first end portion 371 and a second end portion 372. The first end portion 371 of the second coupling member 365 is rotatably coupled to the proximal end portion 312 of the target member 310 via any suitable coupling joint at location 365. The second end portion 372 of the second coupling member 365 is coupled to the proximal end portion 355 of the dilator 354. In this manner, the dilator 354 can rotate relative to the target member 310 about the location 365 independently from the rotation of the sheath 352 relative to the target member 310. Although the sheath 352 and the dilator 354 are both shown as being rotatably coupled to the proximal portion 312 of the target member 310 at location 365, in other embodiments, the sheath 352 and the dilator 354 can be rotatably coupled to the target member 310 at different locations and/or via different coupling joints.

As shown in FIG. 8, the implant insertion device 300 can be placed in a first configuration by disposing the target probe 314 into the body B such that the distal tip 316 of the target probe 314 is adjacent the target tissue T. Said another way, when the implant insertion device 300 is in the first configuration, the distal tip 316 of the target probe 314 is positioned at a predetermined location (e.g., proximate a particular anatomical structure, at a desired depth or the like) within the patient's body B. Moreover, when the implant insertion device 300 is in the first configuration, the contact surface 320 of the anchoring portion 328 can engage the skin S to maintain a position of the target portion 310 relative to the skin S.

When the implant insertion device 300 is in the first configuration, the dilator 354 is disposed within the sheath 352 such that the distal end portion 356 of the dilator 354 is disposed outside of the distal end portion 343 of the sheath 352. In this manner, the sheath 352 and the dilator 356 can be rotated simultaneously relative to the target portion 310 such that the distal end portion 343 of the sheath 352 and the distal end portion 356 of the dilator 354 are moved from a location outside of the body B to a location within the body B adjacent the target tissue T, as shown in FIG. 8. Said another way, when the implant insertion device 300 is in the first configuration, the sheath 352 and the dilator 354 can be rotated relative to the target portion 310 while maintaining the position of the dilator 354 within the sheath 352. In this manner, the sheath 352 and the dilator 354 can cooperatively define an incision (not identified in FIGS. 8-10) in the skin S and/or a passageway (not identified in FIGS. 8-10) within the body B. In some embodiments, the position of the dilator 354 within the sheath 352 can be maintained by a detent, a biasing member, a locking mechanism and/or the like.

As shown in FIG. 9, the implant insertion device 300 can be placed in the second configuration by rotating the dilator 354 relative to the target portion 310 as shown by the arrow GG such that the dilator 354 is disposed entirely outside of the lumen 353 of the sheath 352. Said another way, when the implant insertion device 300 is moved between the first configuration and the second configuration, the dilator 354 is rotated relative to the target portion 310 while the sheath 352 remains at a constant position relative to the target portion 310. Said yet another way, when the implant insertion device 300 is moved between the first configuration and the second configuration, the dilator 354 is rotated relative to the target portion 310 independently from the sheath 352.

When the implant insertion device 300 is in the second configuration, an implant 302 is disposed within the lumen 353 of the sheath 352 at the proximal end portion 342 of the sheath 352. The implant 302 includes a proximal end portion 303 and a distal end portion 305. As shown in FIG. 9, the distal end portion 305 of the implant 302 is disposed first into the lumen 353 and is tapered such that the distal end portion 305 can pierce, dilate and/or displace bodily tissue. As described above, the implant 302 can be an electronic implant, such as, for example, a microstimulator, an elongate implant, an electronic lead, an electrode, a power supply, an amplifier and/or a sensor.

When the implant insertion device 300 is moved between the second configuration (FIG. 9) and the third configuration (FIG. 10), the dilator 354 is rotated relative to the target portion 310 as shown by the arrow HH in FIG. 10. In this manner, the distal end portion 356 of the dilator 354 is disposed within the lumen 353 of the sheath 354 and is in contact with the proximal end 303 of the implant 302. Accordingly, the movement of the dilator 354 within the sheath 352 causes the implant 302 to move within the lumen 353 until the implant 302 is disposed within the body B outside of the sheath. Said another way, when the implant insertion device 300 is moved between the second configuration and the third configuration, the implant 302 is moved from a location outside of the body B to a location within the body B adjacent the target tissue T via the sheath 352. In this manner, the sheath 352 can prevent the implant 302 from contacting bodily tissue during the insertion process, thereby reducing the likelihood that the implant 302 will be damaged during the insertion process.

Figure 11:
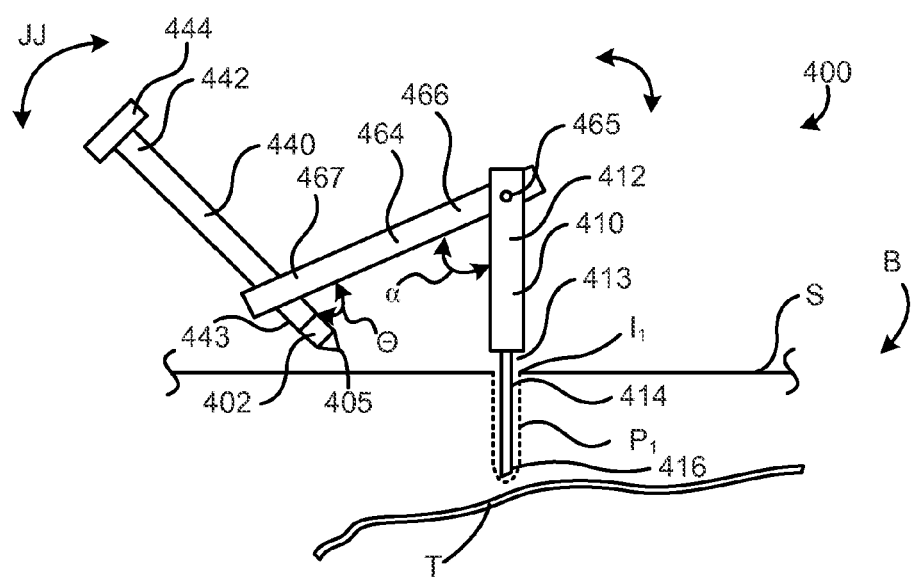
FIGS. 11-13 are front views of a medical device according to an embodiment of the invention in a first configuration, a second configuration, and a third configuration, respectively.
Figure 12:
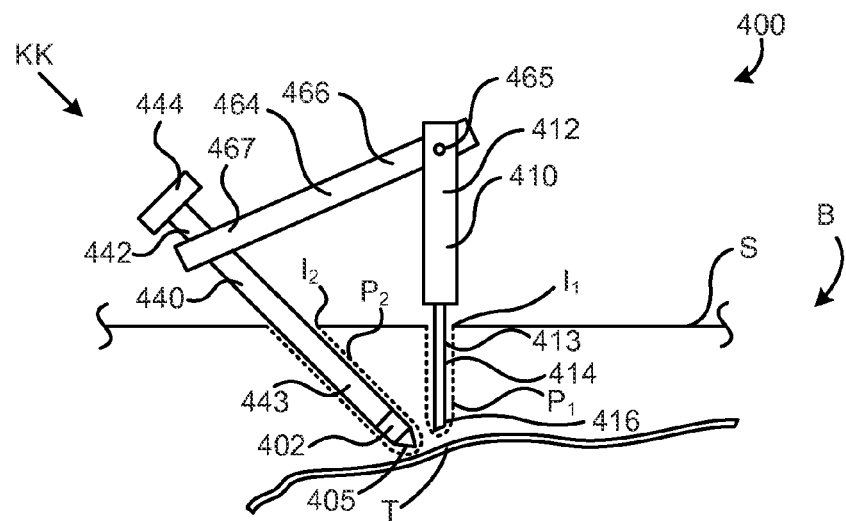
Figure 13:
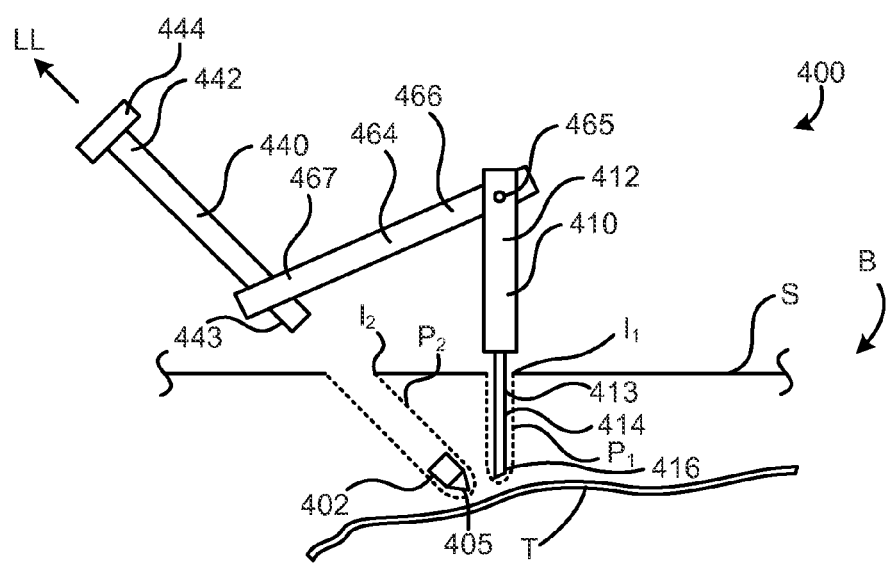

Although the insertion members of the medical devices shown and described above are shown as being rotatably coupled to a target member of the medical device, in other embodiments, an insertion member can by movably coupled to a target member in any suitable fashion. For example, in some embodiments, an insertion member can be coupled to a target member such that the insertion member can translate with respect to the target member. For example, FIGS. 11-13 are front views of a medical device 400 according to an embodiment of the invention in a first configuration, a second configuration, and a third configuration, respectively. The medical device 400 includes a target member 410, an insertion member 440, and a coupling member 464. The target member 410 has a proximal end portion 412 and a distal end portion 413. The distal end portion 413 includes a target probe 414 of the types described herein configured to locate a target tissue T within the body B. For example, in some embodiments, the target probe 414 can be an electronic stimulating probe having an exposed electrode configured to stimulate a muscle, a nerve or the like and/or receive an electronic signal from a muscle, nerve or the like to locate the target tissue T.

The insertion member 440 has a proximal end portion 442 and a distal end portion 443. The distal end portion 443 of the insertion member 440 is selectively coupled to an implant 402. The selective coupling of the distal end portion 443 of the insertion member 440 and the implant 402 can be accomplished by any suitable means, as described above. The implant 402 includes a distal end 405 configured to extend from distal end portion 443 of the insertion member 440. The distal end portion 405 of the implant 402 is tapered such that the distal end portion 405 can pierce, dilate and/or displace bodily tissue. As described above, the implant 402 can be an electronic implant, such as, for example, a microstimulator, an elongate implant, an electronic lead, an electrode, a power supply, an amplifier and/or a sensor.

The proximal end portion 442 of the insertion member 440 includes an actuator 444 configured to selectively couple and/or decouple the distal end portion 443 of the insertion member 440 from the implant 402. As described above, the actuator 444 can be any suitable actuator, such as for example, a mechanical actuator, an electrical actuator, a hydraulic actuator, a pneumatic actuator or the like.

The proximal end portion 442 of the insertion member 440 is movably coupled to the target member 410 by the coupling member 464, which includes a first end portion 466 and a second end portion 467. The first end portion 466 of the coupling member 464 is rotatably coupled to the proximal end portion 412 of the target member 410 at the coupling joint 465. In this manner, the coupling member 464, and therefore the insertion member 440, can rotate relative to the target member 410 about the coupling joint 465, as shown by the arrow II in FIG. 11. Said another way, the coupling member 464 can rotate relative to the target member 410 to change the angle $\alpha$ (identified in FIG. 11) between the coupling member 464 and the target member 410.

Similarly, the second end portion 467 of the coupling member 464 is movably coupled to the proximal end portion 442 of the insertion member 440 such that the insertion member 440 can translate and rotate relative to the target member 410 and/or the coupling member 464. In this manner, the insertion member 440 can rotate relative to the target member 410 independent from the rotation of the coupling member 464 relative to the target member 410, as shown by the arrow JJ in FIG. 11. Similarly stated, the insertion member 440 can rotate relative to the coupling member 464 to change the angle $\Theta$ (identified in FIG. 11) between the insertion member 440 and the coupling member 464. Moreover, as described in more detail below, the insertion member 440 can translate relative to the target member 410 and/or the coupling member 464 as shown by arrow KK in FIG. 12. Similarly stated, the insertion member 440 can move relative to the target member 410 and/or the coupling member 464 without the angular orientation of the insertion member 440 relative to the target member 410 and/or the coupling member 464 changing.

As shown in FIG. 11, the medical device 400 can be placed in the first configuration by inserting the distal end portion 413 of the target member 410 into the body B through a first incision $I_1$ in the skin S. The distal end portion 413 is inserted via a first passageway $P_1$ such that the distal tip 416 of the target probe 414 is adjacent the target tissue T. When the medical device 400 is in the first configuration, the distal end portion 443 of the insertion member 440 is coupled to the implant 402. Additionally, the insertion member 440 is in a first position relative to the target member 410 and/or the coupling member 464 such that the distal end portion 443 of the insertion member 440 is disposed outside of the body B. Similarly stated, when the medical device 400 is in the first configuration, the coupling member 464 is at an angular orientation relative to the target member 410 as defined by the angle α and the insertion member 440 is at an angular orientation relative to the coupling member 464 as defined by the angle Θ. The angular orientation of the insertion member 440 relative to the target member 410 can be adjusted and/or maintained, as described above. In this manner, the user can define a predetermined location for the incision and/or a predetermined trajectory of the passageway $P_2$ through which the distal end portion 443 of the insertion member 440 will be inserted into the body B.

The medical device 400 can be moved from the first configuration (FIG. 11) to the second configuration (FIG. 12) by translating the insertion member 440 relative to the coupling member 464 and/or the target member 410, as shown by the arrow KK in FIG. 12. Said another way, the medical device 440 can be moved from the first configuration to the second configuration by moving the insertion member 440 relative to the coupling member 464 such that the angular orientation of the insertion member 440 relative to the coupling member 464 does not change. When the medical device 400 is moved between the first configuration and the second configuration, the distal end portion 443 of the insertion member 440 is inserted into the body B through a second incision $I_2$ in the skin S. The distal end portion 443 of the insertion member 440 is moved within the body B via a second passageway $P_2$ such that the distal end portion 443 of the insertion member 440 is adjacent the target tissue T and/or the distal end portion 416 of the target probe 414. Accordingly, when the medical device 400 is moved between the first configuration and the second configuration, the implant 402 is moved from a region outside of the body to a region within the body B.

When the distal end portion 443 of the insertion member 440 and/or the implant 402 is adjacent the target tissue T, the distal end portion 443 of the insertion member 440 can be decoupled from the implant 402 using the actuator 444. The insertion member 440 can then be translated relative to the target member 410 and/or the coupling member 464 as shown by the arrow LL in FIG. 13, thereby placing the medical device 400 in the third configuration. When the medical device 400 is moved between the second configuration (FIG. 12) and the third configuration (FIG. 13), the distal end portion 443 of the insertion member 440 is removed from within the body B via the second passageway $P_2$ and the second incision $I_2$, while the implant 402 remains within the body B.

Figure 14:
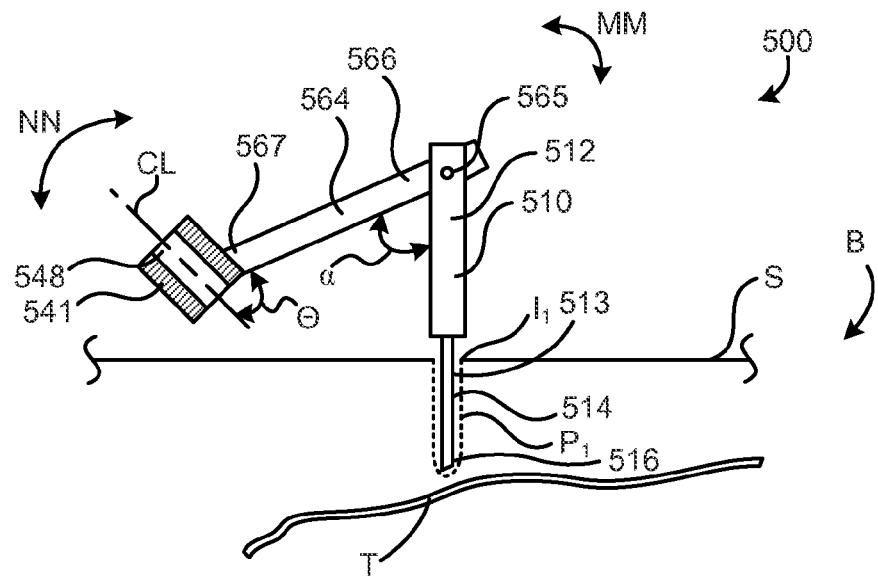
FIGS. 14 and 15 are partial cross-sectional front views of a medical device according to an embodiment of the invention in a first configuration and a second configuration, respectively.
Figure 15:
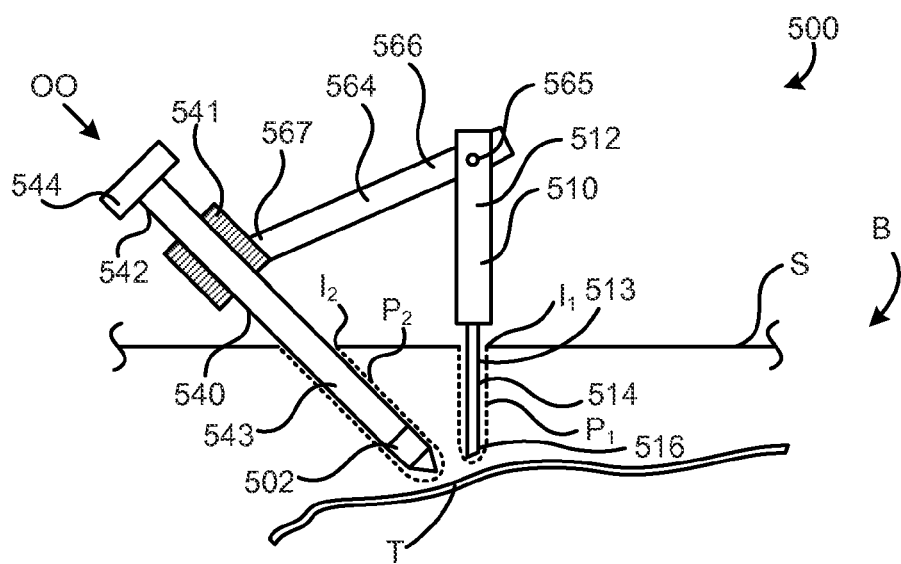

Although the insertion member 440 is shown and described above as being movably coupled to the coupling member 464, in other embodiments, a medical device 440 can include an insertion member 440 that can be slidably disposed within and/or removably coupled to a coupling member 464. For example, FIGS. 14 and 15 are partial cross-sectional front views of a medical device 500 according to an embodiment of the invention. The medical device 500 includes a target member 510, an insertion tool 540, an insertion guide member 541, and a coupling member 564. The target member 510 has a proximal end portion 512 and a distal end portion 513. The distal end portion 513 includes a target probe 514 of the types described herein configured to locate a target tissue T within the body B.

The insertion guide member 541 defines a lumen 548 therethrough. The lumen 548 defines a center line CL. As described in more detail herein, the lumen 548 is configured to receive a portion of the insertion tool 540. The insertion guide member 541 is movably coupled to the target member 510 by the coupling member 564, which includes a first end portion 566 and a second end portion 567. The first end portion 566 of the coupling member 564 is rotatably coupled to the proximal end portion 512 of the target member 510 at the coupling joint 565. In this manner, the coupling member 564, and therefore the insertion tool 540, can rotate relative to the target member 510 about the coupling joint 565, as shown by the arrow MM in FIG. 14. Said another way, the coupling member 564 can rotate relative to the target member 510 to change the angle α (identified in FIG. 14) between the coupling member 564 and the target member 510.

Similarly, the second end portion 567 of the coupling member 564 is rotatably coupled to the insertion guide member 541. In this manner, the insertion guide member 541 can rotate relative to the target member 510 independent from the rotation of the coupling member 564 and relative to the target member 510, as shown by the arrow NN in FIG. 14. Similarly stated, the insertion guide member 541 can rotate relative to the coupling member 564 to change the angle Θ (identified in FIG. 14) between the insertion guide member 541 and the coupling member 564.

The insertion tool 540 has a proximal end portion 542 and a distal end portion 543. The distal end portion 543 of the insertion tool 540 is selectively coupled to an implant 502. The selective coupling of the distal end portion 543 of the insertion tool 540 and the implant 502 can be accomplished by any suitable means, as described above. As described above, the implant 502 can be an electronic implant, such as, for example, a microstimulator, an elongate implant, an electronic lead, an electrode, a power supply, an amplifier and/or a sensor. The proximal end portion 542 of the insertion tool 540 includes an actuator 544 configured to selectively couple and/or decouple the distal end portion 543 of the insertion tool 540 from the implant 502. As described above, the actuator 544 can be any suitable actuator, such as for example, a mechanical actuator, an electrical actuator, a hydraulic actuator, a pneumatic actuator or the like.

As shown in FIG. 14, the medical device 500 can be placed in the first configuration by inserting the distal end portion 513 of the target member 510 into the body B through a first incision $I_1$ in the skin S. The distal end portion 513 is inserted via a first passageway $P_1$ such that the distal tip 516 of the target probe 514 is adjacent the target tissue T. When the medical device 500 is in the first configuration, the insertion guide member 541 is in a predetermined position and/or angular orientation relative to the coupling member 564 and/or the target member 510. Similarly stated, when the medical device 500 is in the first configuration, the coupling member 564 is at an angular orientation relative to the target member 510 as defined by the angle α and the insertion guide member 541 is at an angular orientation relative to the coupling member 564 by the angle Θ. In this manner, the user can define a predetermined location for the incision and/or a predetermined trajectory of the passageway $P_2$ through which the distal end portion 543 of the insertion tool 540 will be inserted into the body B.

When the medical device 500 is in the first configuration, the insertion tool 540 is decoupled from the insertion guide member 541. Said another way, the when the medical device 500 is in the first configuration, the insertion tool 540 is disposed outside of the lumen 548 defined by the insertion guide member 541.

The medical device 500 can be moved from the first configuration (FIG. 14) to the second configuration (FIG. 15) by inserting the distal end portion 543 of the insertion tool 540 within the lumen 548 and sliding the insertion tool 540 distally as shown by the arrow OO in FIG. 15. Said another way, the medical device 540 can be moved from the first configuration to the second configuration by translating at least a portion of the insertion tool 540 within the insertion guide member 541. When the medical device 500 is moved between the first configuration and the second configuration, the distal end portion 543 of the insertion tool 540 is inserted into the body B through a second incision I₂ in the skin S. The distal end portion 543 of the insertion tool 540 is moved within the body B via a second passageway P₂ such that the distal end portion 543 of the insertion tool 540 is adjacent the target tissue T and/or the distal end portion 516 of the target probe 514. Accordingly, when the medical device 500 is moved between the first configuration and the second configuration, the implant 502 is moved from a region outside of the body to a region within the body B.

Figure 16:
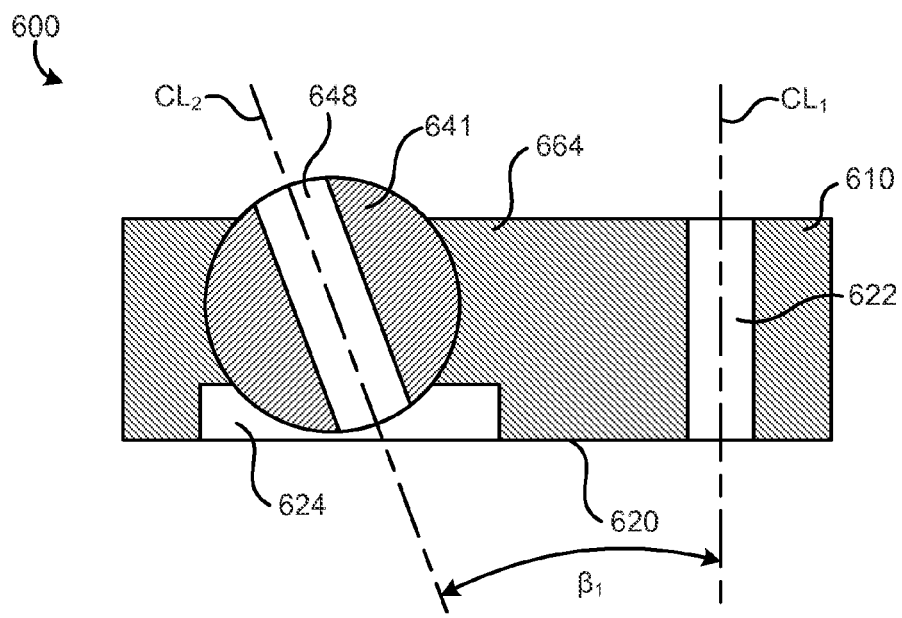
FIGS. 16-18 are cross-sectional front views of a medical device according to an embodiment of the invention in a first configuration, a second configuration, and a third configuration, respectively.
Figure 17:
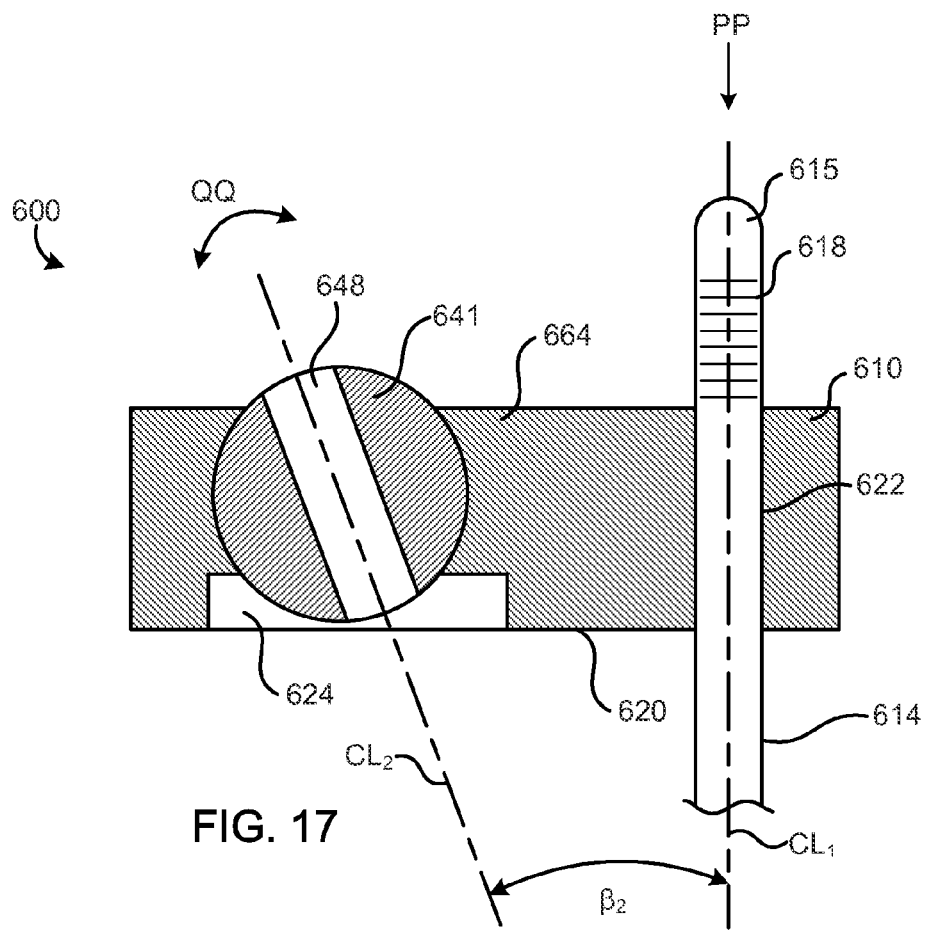
Figure 18:
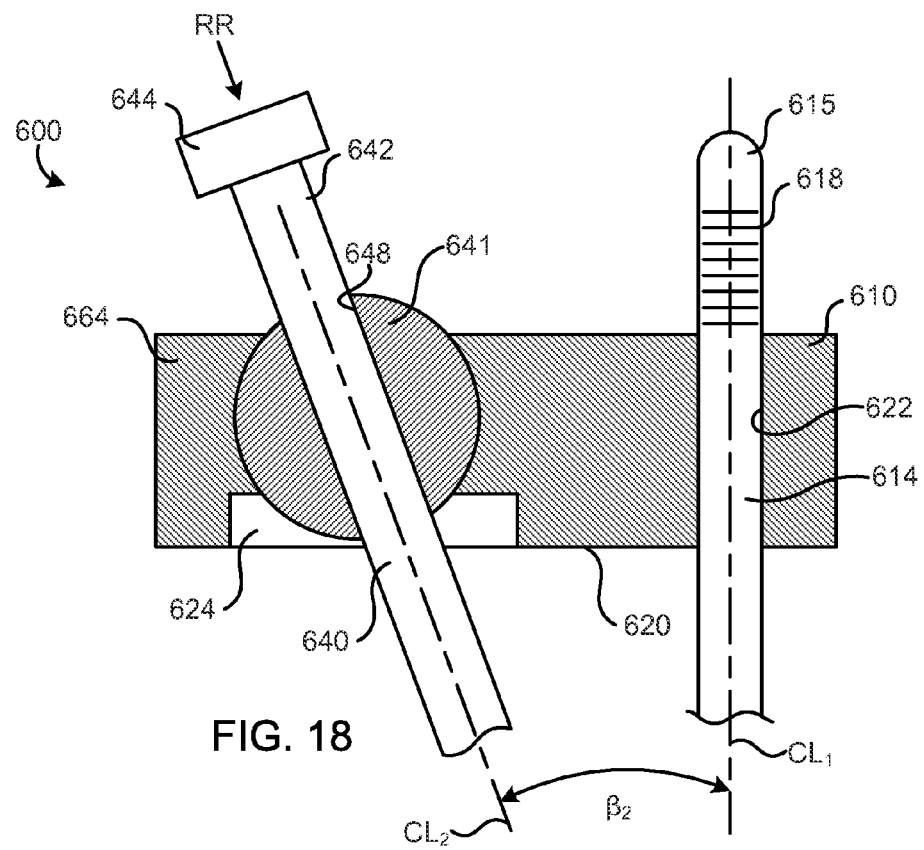

When the distal end portion 543 of the insertion tool 540 and/or the implant 502 is adjacent the target tissue T, the distal end portion 543 of the insertion tool 540 can be decoupled from the implant 502 using the actuator 544. The insertion tool 540 can then be translated relative to the insertion guide member 541 to remove the distal end portion 543 of the insertion tool 540 from the body B FIGS. 16-18 are cross-sectional front views of a target device 600 according to an embodiment of the invention, in a first configuration, a second configuration and a third configuration, respectively. The target device 600 includes a target portion 610 and an insertion portion 664. The target portion 610 of the target device 600 includes a contact surface 620 configured to be disposed against and/or anchored to the skin of a body (not shown in FIGS. 16-18). The target portion 610 of the target device 600 defines a first lumen 622 having a center line CL₁.

The insertion portion 664 of the target device 600 includes an insertion guide member 641. The insertion guide member 641 defines a second lumen 648 having a center line CL₂. At least a portion of the insertion guide member 641 is disposed within a cavity 624 defined by the insertion portion 664 of the target device 600 such that the insertion guide member 641 can rotate relative to the target device 600, as shown by the arrow QQ in FIG. 17. Said another way, the insertion can rotate relative to the target device 600 such that an angle β between the center line CL₁ of the first lumen 622 and the center line CL₂ of the second lumen 648 can be changed. Said yet another way, the insertion guide member 641 is configured to rotate within the cavity 624 about an axis substantially normal to the center line CL₁ and/or the center line CL₂. Although the insertion guide member 641 is shown in FIGS. 16 and 17 as rotating about a single axis, in other embodiments, the insertion guide member 641 can rotate about multiple axes. For example, in some embodiments, the insertion guide member 641 can have a spherical shape that corresponds to a spherical shape of the cavity 624 (i.e., the insertion guide member 641 and the cavity 624 can form a ball-and-socket joint).

In use, the target device 600 can be placed against the body (not shown in FIGS. 16-18) to guide the insertion of an implant. As shown in FIG. 17, when the target device 600 is in the second configuration, a target probe 610 of the types shown and described herein can be disposed within the first lumen 622 such that a distal tip (not shown in FIGS. 16-18) of the target probe 614 extends distally outside of the first lumen 622. Similarly stated, when the target device 600 is in the second configuration, a portion of the target probe 614 is disposed within the first lumen 622 such that the distal tip of the target probe 614 is disposed outside of the first lumen 622 on the distal side of the target device 600 and a proximal end portion 615 of the target probe 614 is disposed outside of the first lumen 622 on the proximal side of the target device 600.

The target probe 614 is configured to move within the first lumen 622 as shown by the arrow PP in FIG. 17. Similarly stated, when the target device 600 is moved from the first configuration (FIG. 16) to the second configuration (FIG. 17), the target probe 614 is moved within the first lumen 622 along the center line CL₁. Accordingly, in a similar manner as described above, a portion of the target probe 614 can be inserted into the body such that the distal tip of the target probe 614 is adjacent to a target tissue (not shown in FIGS. 16-18). Said another way, when the target probe 614 is inserted into the body, the target device 614 is guided by the first lumen 622 of the target device 600.

The proximal end portion 615 includes multiple graduated markings 618 that indicate the position of the target probe 614 relative to the target portion 610 of the target device 600. Similarly stated, the graduated markings 618 of the proximal end portion 615 can indicate the distance between the distal tip of the target probe 614 and the contact surface 620 of the target device 600. In this manner, as described above with reference to FIG. 5, the graduated markings 618 can indicate the depth of the insertion of the target probe 614.

As described above, in some instances, locating the target tissue with the target probe 614 can be an iterative process. Accordingly, in some embodiments, the distal tip of the target probe 614 can be inserted into the body before target probe 614 is disposed within the first lumen 622. In this manner, the target tissue can be located before the contact surface 620 is placed against and/or anchored to the skin. In such embodiments, after the distal tip of the target probe 614 is within the body, the target device 600 can be moved about the target probe 614 until the contact surface 620 is disposed against the body.

When the target device 600 is moved between the first configuration and the second configuration, the insertion guide member 641 is rotated such that the angle between the center line CL₁ of the first lumen 622 and the center line CL₂ of the second lumen 648 is changed from β₁ to β₂. In some embodiments, the magnitude of the rotation of the insertion guide member 641 can be indicated by a series of graduated markings (not shown in FIGS. 16-18) on the surface of the insertion guide member 641.

The target device 600 can be moved from the second configuration (FIG. 17) to the third configuration (FIG. 18) by inserting a portion of an insertion tool 640 into the second lumen 648. Said another way, when the target device 600 is moved from the second configuration to the third configuration, at least a portion of the insertion tool 640 is translated relative to the target device 600 as shown by the arrow RR in FIG. 18. Similarly stated, when the target device 600 is moved from the second configuration to the third configuration, the movement of the insertion tool 640 is guided by the second lumen 648 of the target device 600.

The insertion tool 640 can be similar to the insertion tools shown and described above, and can include a distal end portion (not shown in FIG. 18) configured to be selectively coupled to an implant (not shown in FIG. 18). The insertion tool 640 also includes a proximal end portion 642 that includes an actuator 644 of the types shown and described above. Accordingly, when the insertion tool 640 is moved within the second lumen 648, the distal end portion of the insertion tool 640 can be inserted into the body. The distal end portion of the insertion tool 640 can be moved within the body B such that the distal end portion of the insertion tool 640 is adjacent the target tissue and/or the distal tip of the target probe 614. Accordingly, when the target device 600 is moved between the second configuration and the third configuration, the implant can be moved from a region outside of the body to a region within the body B.

Figure 19:
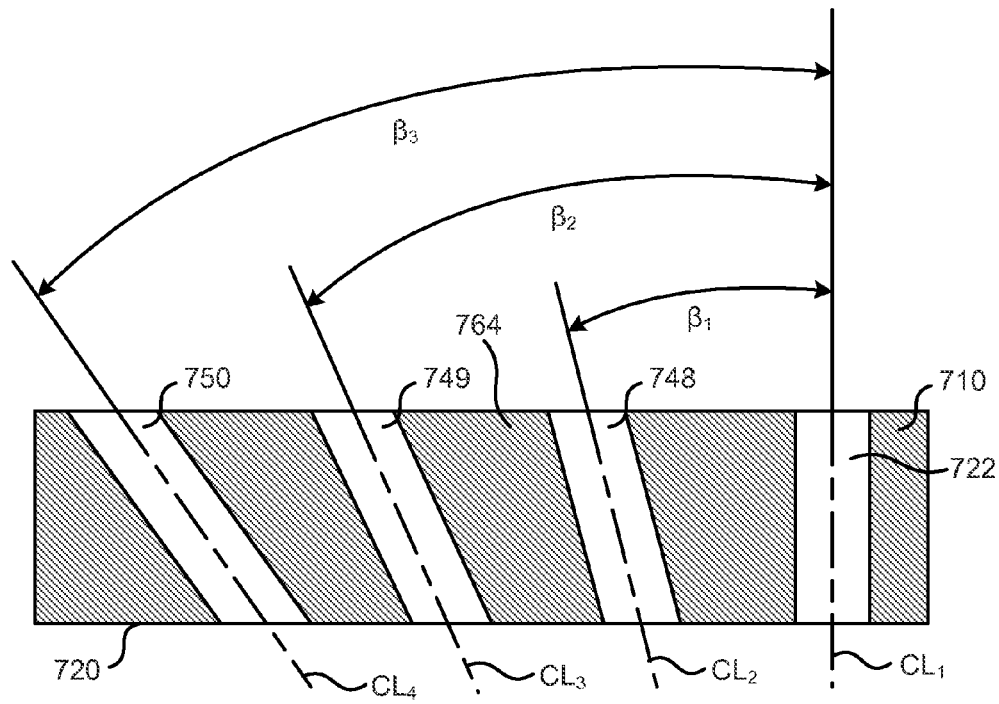
FIG. 19 is a cross-sectional front view of a medical device according to an embodiment of the invention.

Although the insertion guide member 641 of the target device 600 is shown as being movable relative to the target portion 610 of the guide member 600, in other embodiments, a target device can include an insertion guide portion that maintained in a fixed position and/or orientation. For example, FIG. 19 is a cross-sectional view of a target device 700 according to an embodiment of the invention. The target device 700 includes a target portion 710 and an insertion portion 764. The target portion 710 of the target device 700 includes a contact surface 720 configured to be disposed against and/or anchored to the skin of a body (not shown in FIG. 19). The target portion 710 of the target device 700 defines a first lumen 722 having a center line $CL_1$.

The insertion portion 764 of the target device 700 defines a second lumen 748, a third lumen 749, and a fourth lumen 750. The second lumen has a center line $CL_2$ that is angularly offset from the center line $CL_1$ by a constant angle $\beta_1$. Said another way, the center line $CL_2$ is non parallel to the center line $CL_1$. Similarly, the third lumen has a center line $CL_3$ that is angularly offset from the center line $CL_1$ by a constant angle $\beta_2$ that is different from the angle $\beta_1$. Said another way, the center line $CL_3$ is non parallel to the center lines $CL_1$ and $CL_2$. Similarly, the fourth lumen has a center line $CL_4$ that is angularly offset from the center line $CL_1$ by a constant angle $\beta_3$ that is different from the angles $\beta_1$ and $\beta_2$. Said another way, the center line $CL_4$ is non parallel to the center lines $CL_1$, $CL_2$, and $CL_3$.

In use, the target device 700 can be placed against the body (not shown in FIG. 19) and used to guide the insertion of a target probe and an insertion tool in a similar manner as described above with reference to FIGS. 16-18. More particularly, the first lumen 722 can receive and/or guide the insertion of the target probe into the body. The insertion tool can inserted into the body via any one of the second lumen 748, the third lumen 749, and/or the fourth lumen 750 according to the desired insertion location and/or trajectory of insertion path.

Figure 20:
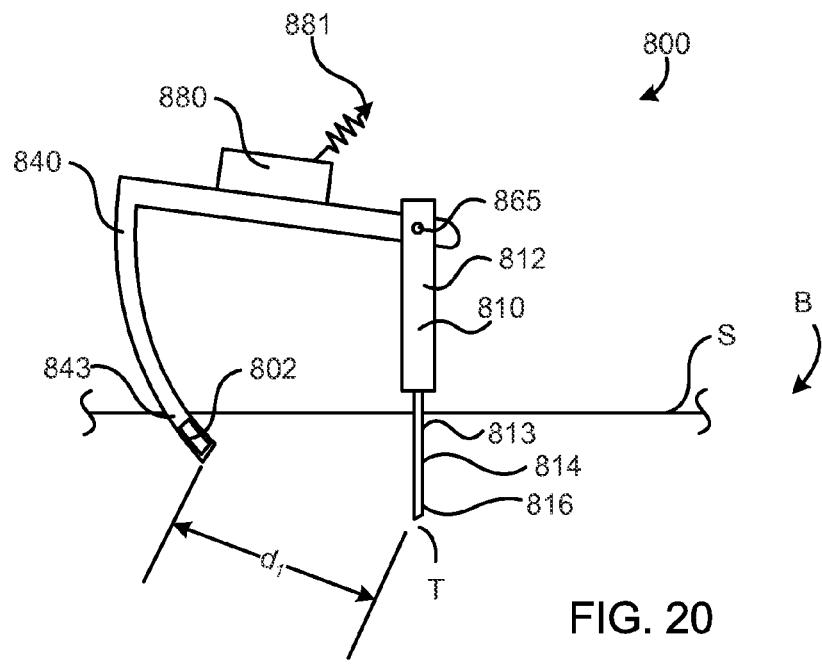
FIGS. 20 and 21 are schematic illustrations of a medical device according to an embodiment of the invention in a first configuration and a second configuration, respectively.
Figure 21:
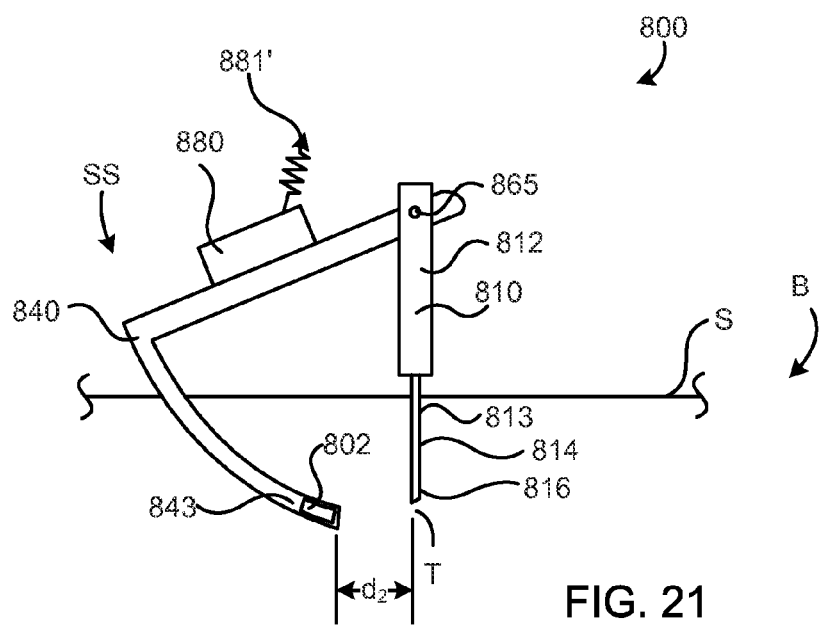

FIGS. 20 and 21 are schematic illustrations of a medical device 800 according to an embodiment of the invention in a first configuration and a second configuration, respectively. The medical device 800 includes a target member 810, an insertion member 840, and an electronic circuit system 880. The target member 810 has a proximal end portion 812 and a distal end portion 813. The distal end portion 813 includes a target probe 814 configured to locate a target tissue T within the body B. For example, in some embodiments, the target probe 814 can be an electronic stimulating probe having an exposed electrode configured to stimulate a muscle, a nerve or the like and/or receive an electronic signal from a muscle, nerve or the like to locate the target tissue T.

The insertion member 840 has a proximal end portion 842 and a distal end portion 843. The distal end portion 843 of the insertion member 840 is configured to be selectively coupled to an implant 802, as described above. In some embodiments, for example, the implant 802 can be an electronic implant, such as, for example, a microstimulator, an elongate implant, an electronic lead, an electrode, a power supply, an amplifier and/or a sensor. In other embodiments, the implant 802 can be devoid of electronic circuitry, such as, for example, a drug-eluting implant. The proximal end portion 842 of the insertion member 840 is rotatably coupled to the proximal end portion 812 of the target member 810 at a coupling joint 865. In this manner, the insertion member 840 can rotate relative to the target member 810 about the coupling joint 865. Accordingly, the medical device 800 is configured to insert the implant 802 into the body B, as described above.

The electronic circuit system 880 is coupled to the proximal end portion 842 of the insertion member 840. The electronic circuit system 880 is configured to produce an electronic signal 881 proportional to the distance between the distal end portion 843 of the insertion member 840 and the distal end portion 814 of the target member 810, as described in more detail herein. The electronic signal 881 can include a visual output, an audible output and/or a haptic output. For example, in some embodiments, the electronic signal 881 can be associated with an audible message informing a user of the distance between the distal end portion 843 of the insertion member 840 and the distal end portion 814 of the target member 810. In other embodiments, for example, the electronic signal 881 can be associated with a visual text message indicating the distance between the distal end portion 843 of the insertion member 840 and the distal end portion 814 of the target member 810 (e.g., a numeric read-out indicating the distance in millimeters, inches, or any other desired units of measure).

As shown in FIG. 20 and described above, the distal end portion 813 of the target member 810 can be inserted into the body B through a first incision (not shown in FIGS. 20 and 21) in the skin S. In this manner, a distal tip 816 of the target probe 814 can be positioned at a target location T within the patient's body B (e.g., proximate a particular anatomical structure, at a desired depth or the like). Similarly, as shown in FIG. 20 and described above, the distal end portion 843 of the insertion member 840 and/or the implant 802 can be inserted into the body B, thereby placing the medical device 800 in a first configuration. When the medical device 800 is in the first configuration (FIG. 20), the distal end portion 843 of the insertion member 840 and/or the implant 802 is spaced apart from the distal tip 816 of the target probe 814 by a distance $d_1$. Moreover, when the medical device 800 is in the first configuration, the electronic signal 881 produced by the electronic circuit system 880 is proportional to the distance $d_1$.

As described above, the distal end portion 843 of the insertion member 840 and/or the implant 802 can be moved within the body B by rotating the insertion member 840 relative to the target member 810 as shown by the arrow SS in FIG. 21. In this manner, the medical device 800 can be moved from the first configuration to the second configuration within the body B. When the medical device 800 is in the second configuration (FIG. 21), the distal end portion 843 of the insertion member 840 and/or the implant 802 is spaced apart from the distal tip 816 of the target probe 814 by a distance $d_2$. Moreover, when the medical device 800 is in the second configuration, the electronic signal 881' produced by the electronic circuit system 880 is proportional to the distance $d_2$. In this manner, the user can move the distal end portion 843 of the insertion member 840 and/or the implant 802 within the body B in response to the electronic signals 881, 881'. Said another way, the user can move the implant 802 from a region outside of the body to a region within the body adjacent the target location T in response to the electronic signals 881, 881'. Said yet another way, the user can use the electronic signals 881, 881' to guide the placement of the implant 802 within the body B.

The electronic circuit systems shown and described above can include many electronic components operatively coupled to perform the functions described herein For example, in some embodiments, the electronic circuit system 880 can include a processor operatively coupled to a memory device (the components that can be included in the electronic circuit system 880, such as the processor and the memory device, are not shown in FIGS. 20 and 21). The memory device can be configured to store processor-readable code instructing the processor to perform the functions described herein. In some embodiments, the electronic circuit system 880 can include an input/output device configured to receive electronic inputs from an electrode, as described in more detail below. In some embodiments, the input/output device can receive one or more inputs from any suitable source, such as, for example, the user's voice (e.g., through a microphone), a keyboard, a touch screen, a proximity sensor and/or the like. The input/output device can also configured to produce and/or output the electronic signal 881, 881' to various output devices, such as, for example, a visual output device, an audio output device, and/or a haptic output device.

The processor that can be included within the electronic circuit system 880 can be a commercially-available processing device dedicated to performing one or more specific tasks. For example, in some embodiments, the processor can be a commercially-available microprocessor. Alternatively, the processor can be an application-specific integrated circuit (ASIC) or a combination of ASICs, which are designed to perform one or more specific functions. In yet other embodiments, the processor can be an analog or digital circuit, or a combination of multiple circuits.

Figure 22:
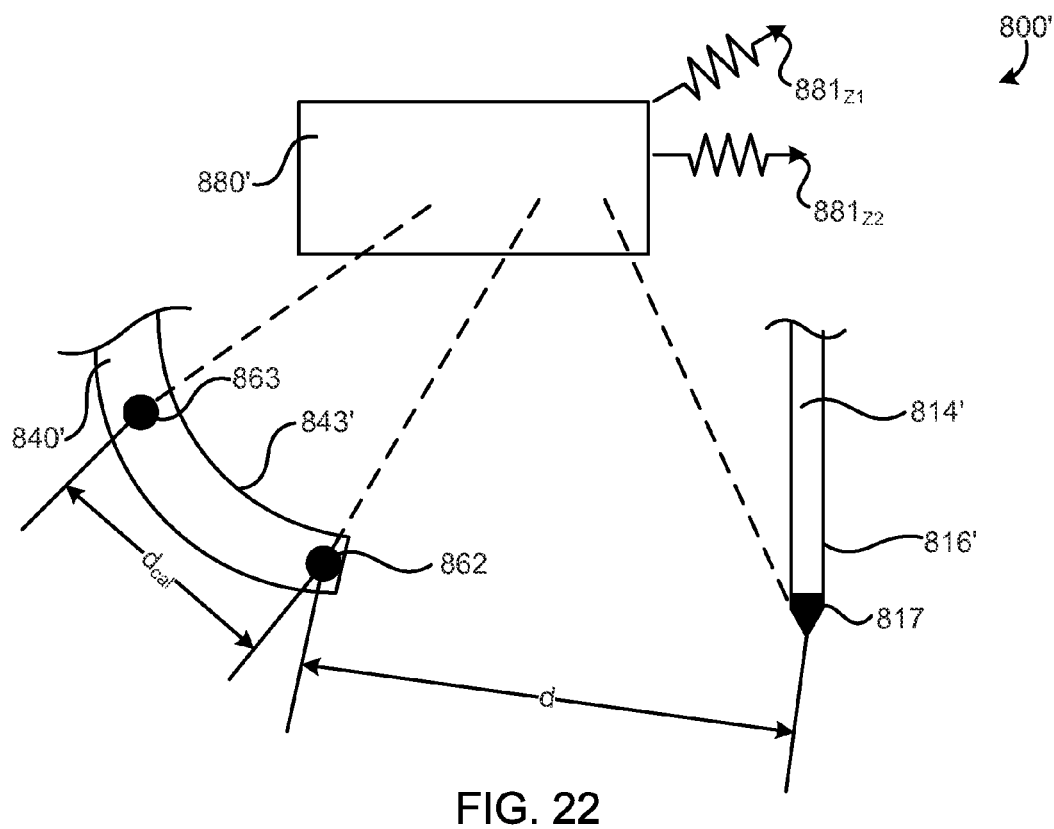
FIG. 22 is a schematic illustration of a portion of a medical device according to an embodiment of the invention.

The electronic signals 881, 881' can be associated with any suitable electrical characteristic and/or material property of the bodily tissue disposed between the distal end portion 843 of the insertion member 840 and/or the implant 802 and the distal tip 816 of the target probe 814. For example, in some embodiments, the electronic signals 881, 881' can be associated with an impedance between the distal tip 816 of the target probe 814 and the distal end portion 843 of the insertion member 840, a resistance between the distal tip 816 of the target probe 814 and the distal end portion 843 of the insertion member 840, a capacitance between the distal tip 816 of the target probe 814 and the distal end portion 843 of the insertion member 840, and/or an inductance between the distal tip 816 of the target probe 814 and the distal end portion 843 of the insertion member 840. For example, FIG. 22 is a schematic illustration of a portion of a medical device 800' configured to produce electronic signals $881_{Z1}$, $881_{Z2}$ associated with an impedance between the distal tip 816 of the target probe 814 and the distal end portion 843 of the insertion member 840. Similar to the medical device 800 described above with reference to FIGS. 21 and 22, the medical device 800' includes a target probe 814', an insertion member 840', and an electronic circuit system 880'. The target probe 814' has a distal tip 816' that includes an electrode 817 that is electronically coupled to and/or is included within the electronic circuit system 880, as indicated by the dashed lines in FIG. 22.

The insertion member 840' includes a distal end portion 843' that can be selectively coupled to an implant (not shown in FIG. 22), as described above. The distal end portion 843' of the insertion member 840' includes a first electrode 862 and a second electrode 863 spaced apart by a distance $d_{cal}$. The first electrode 862 and the second electrode 863 are electronically coupled to and/or are included within the electronic circuit system 880, as indicated by the dashed lines in FIG. 22.

When the distal end portion 843' of the insertion member 840' is disposed within the body (not shown in FIG. 22), the electronic circuit system 880' is configured to measure the impedance Z1 between the first electrode 862 and the second electrode 863. Based on the impedance Z1 and the known distance dcal, the electronic circuit system 880' can determine a characteristic impedance of the bodily tissue adjacent the distal end portion 843' of the insertion member 840'. The characteristic impedance of the bodily tissue can be used to indicate the type of tissue within which the distal end portion 843' of the insertion member 840' is disposed and/or to define a calibration coefficient for determining the distance d between the distal end portion 843' of the insertion member 840' and the distal tip 816' of the target probe 814', as described below. Accordingly, the electronic circuit system 880 can produce an electronic signal $881_{Z1}$ associated with the impedance Z1.

When the distal end portion 843' of the insertion member 840' and the distal tip 816' of the target probe 814' are disposed within the body, the electronic circuit system 880' is configured to measure the impedance Z2 between the first electrode 862 and/or the second electrode 863 and the electrode 817 of the target probe 814'. The electronic circuit system 880' can then determine the distance d between the distal end portion 843' of the insertion member 840' and the distal tip 816' of the target probe 814' based on the impedance Z2 and the characteristic impedance of the bodily tissue. For example, in some embodiments, the distance d can be determined based on the following formula:

$$d = d_{cal} * (Z2/Z1)$$

Accordingly, the electronic circuit system 880 can produce an electronic signal $881_{Z2}$ associated with the impedance Z2. In other embodiments, the distance d can be determined based on any suitable formula or algorithm. For example, in some embodiments, the distance d can be determined based on a nonlinear function of the impedance Z2. In other embodiments, the distance d can be determined based on a predetermined calibration table that includes an array of values for the impedance Z2.

Figure 23:
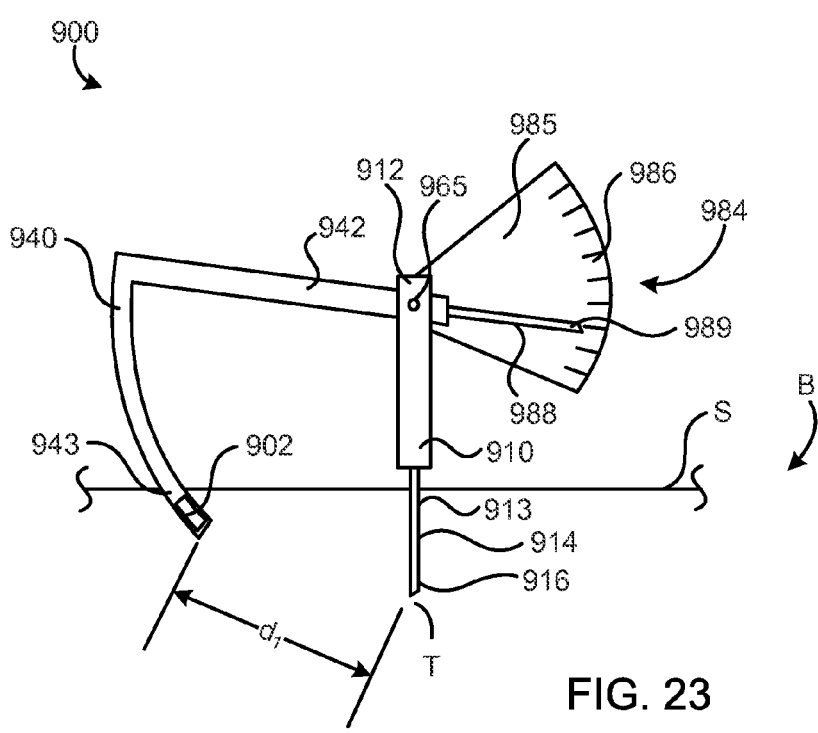
FIGS. 23 and 24 are front views of a medical device according to an embodiment of the invention in a first configuration and a second configuration, respectively.
Figure 24:
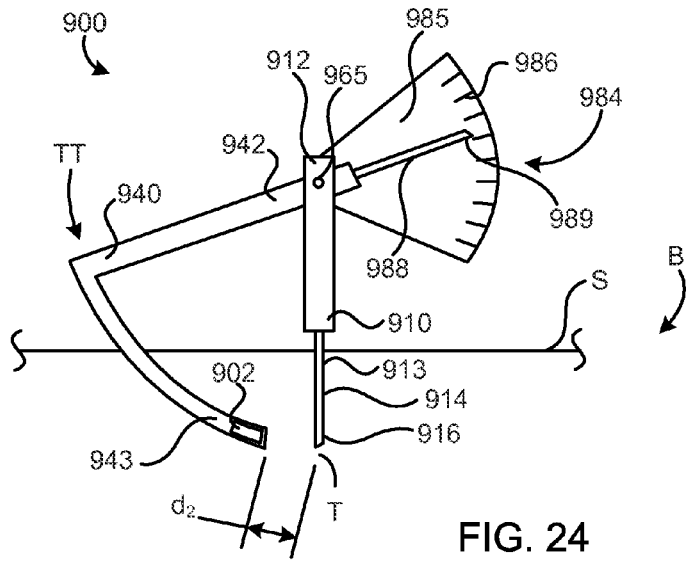

Although the medical device 800 is shown and described above as including an electronic circuit system 880 configured to produce an indication of the position of the distal end portion 843 of the insertion member 840, in other embodiments, a medical device can be configured to produce a non-electronic indication of the position of an insertion member and/or an implant within the body. For example, FIGS. 23 and 24 are front views of a medical device 900 according to an embodiment of the invention. The medical device 900 includes a target member 910, an insertion member 940, and a position indicator 984. The target member 910 has a proximal end portion 912 and a distal end portion 913. The distal end portion 913 includes a target probe 914 configured to locate a target tissue T within the body B. For example, in some embodiments, the target probe 914 can be an electronic stimulating probe having an exposed electrode configured to stimulate a muscle, a nerve or the like and/or receive an electronic signal from a muscle, nerve or the like to locate the target tissue T.

The insertion member 940 has a proximal end portion 942 and a distal end portion 943. The distal end portion 943 of the insertion member 940 is configured to be selectively coupled to an implant 902, as described above. The proximal end portion 942 of the insertion member 940 is rotatably coupled to the proximal end portion 912 of the target member 910 at a coupling joint 965. In this manner, the insertion member 940 can rotate relative to the target member 910 about the coupling joint 965. Accordingly, the medical device 900 is configured to insert the implant 902 into the body B, in a similar manner as described above.

The position indicator 984 includes a gage portion 985 and an arm portion 988. The gage portion 985 is coupled to the proximal end 912 of the target member 910 and includes a series of graduated markings 986. The arm portion 988 is coupled to the proximal end 942 of the insertion member 940 and includes a pointer 989. The pointer 989 is configured to be selectively disposed adjacent one of the graduated markings 986 in response to the position of the distal end portion 943 of the insertion member 940 relative to the target probe 914. Said another way, the arm portion 988 is movably coupled to the gage portion 985 such that the pointer 989 can be selectively disposed adjacent one of the graduated markings 986 to indicate the position of the distal end portion 943 of the insertion member 940 relative to the target probe 914.

As shown in FIG. 23 and described above, the distal end portion 913 of the target member 910 can be inserted into the body B through a first incision (not shown in FIGS. 23 and 24) in the skin S. In this manner, a distal tip 916 of the target probe 914 can be positioned at a target location T within the patient's body B (e.g., proximate a particular anatomical structure, at a desired depth or the like). Similarly, as shown in FIG. 23 and described above, the distal end portion 943 of the insertion member 940 and/or the implant 902 can be inserted into the body B, thereby placing the medical device 900 in a first configuration. When the medical device 900 is in the first configuration (FIG. 23), the distal end portion 943 of the insertion member 940 and/or the implant 902 is spaced apart from the distal tip 916 of the target probe 914 by a distance $d_1$. Moreover, when the medical device 900 is in the first configuration, the position indicator 984 produces an indication associated with the distance $d_1$. Similarly stated, when the medical device 900 is in the first configuration, the pointer 989 is disposed adjacent one of the graduated markings 986 that is associated with the distance $d_1$.

As described above, the distal end portion 943 of the insertion member 940 and/or the implant 902 can be moved within the body B by rotating the insertion member 940 relative to the target member 910 as shown by the arrow TT in FIG. 24. In this manner, the medical device 900 can be moved from the first configuration to the second configuration within the body B. When the medical device 900 is in the second configuration (FIG. 24), the distal end portion 943 of the insertion member 940 and/or the implant 902 is spaced apart from the distal tip 916 of the target probe 914 by a distance $d_2$. Moreover, when the medical device 900 is in the second configuration, the position indicator 984 produces an indication associated with the distance $d_2$. Similarly stated, when the medical device 900 is in the first configuration, the pointer 989 is disposed adjacent one of the graduated markings 986 that is associated with the distance $d_2$. In this manner, the user can move the distal end portion 943 of the insertion member 940 and/or the implant 902 within the body B in response to the indications produced by the position indicator 984.

Although the medical device 200 is shown and described above as including one target probe 214, one insertion member 240, and one implant 202, in other embodiments, a medical device can include multiple target probes, multiple insertion members and/or multiple implants. For example, in some embodiments a kit can include a medical device configured to insert an implant similar to the medical device 200 shown and described above. The kit can also include multiple target probes, each having different characteristics (e.g., length, diameter, electrode configuration, tip geometry, etc.). In some embodiments, for example, the kit can include multiple insertion member, each having different characteristics (e.g., size, radius of curvature, electrode configuration, dilation configuration, etc.). Similarly, in some embodiments, the kit can include multiple implants of the types shown and described above.

The medical devices shown and described herein can be constructed from any suitable material or combination of materials. For example, in some embodiments, an insertion member, such as insertion member 240, can be a constructed from a rigid material, such as Nylon, a composite material, a metal alloy or the like. In other embodiments, an insertion member, such as insertion member 240, can be a constructed from a flexible material. In this manner, the radius of curvature of the insertion member can be changed based on the desired passageway within the body along which the implant is to be inserted.

Figure 25:
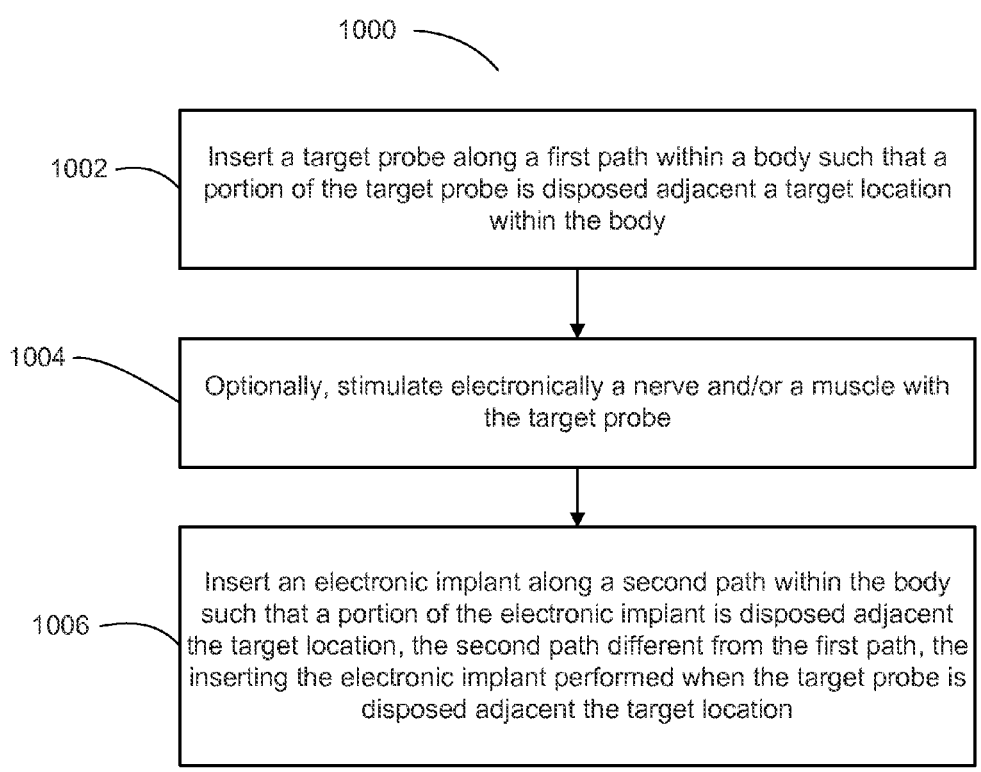
FIGS. 25-28 are flow charts of methods of inserting an implant into a body according to embodiments of the invention.

FIG. 25 is a flow chart of a method 1000 of inserting an implant into a body according to an embodiment of the invention. The method includes inserting a target probe along a first path within a body such that a portion of the target probe is disposed adjacent a target location within the body, 1002. The target probe can be any target probe of the types shown and described above. In some embodiment, for example, target probe can be inserted by disposing a distal end portion of a target portion of an implant delivery device against the body and moving the target probe within the first member of the insertion apparatus such that the portion of the target probe is disposed adjacent the target location.

In some embodiments, the target probe can be an electromyogram (EMG) needle configured to be percutaneously inserted into the body to electrically stimulate and/or receive an electronic signal from the target location within the body. Accordingly, in some embodiments, the method optionally includes stimulating electronically a nerve and/or a muscle with the target probe after the inserting the target probe, 1004.

After the target probe is disposed adjacent the target location, an electronic implant is inserted along a second path within the body such that a portion of the electronic implant is disposed adjacent the target location within the body, 1006. The second path is different from the first path. For example, in some embodiments, a center line of the second path can be non-parallel to a center line of the first path. Moreover, the electronic implant is inserted when the target probe is disposed adjacent the target location within the body.

In some embodiments, the electronic implant is inserted using an implant delivery device of the type shown and described above. For example, in some embodiments, the electronic implant is inserted by moving an insertion member of an implant delivery device relative to the target probe. As described above, the insertion member of the implant delivery device can be selectively coupled the electronic implant.

Figure 26:
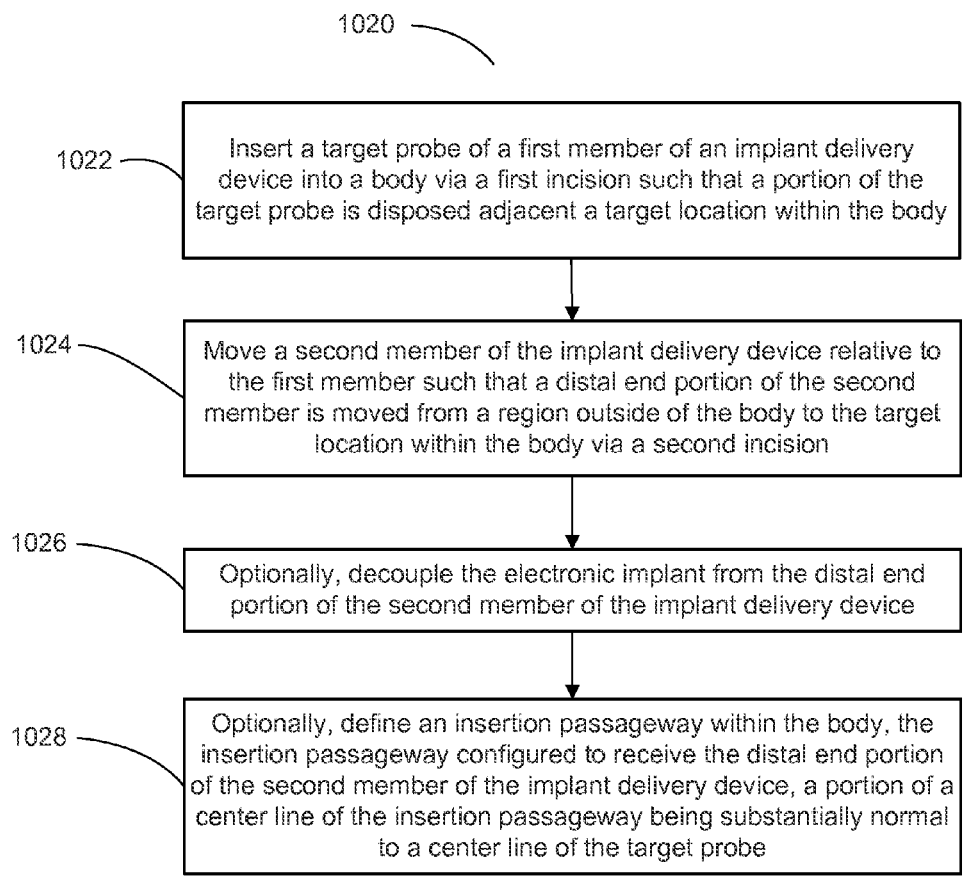

FIG. 26 is a flow chart of a method 1020 of inserting an implant into a body according to an embodiment of the invention. The method includes inserting a target probe of a first member of an implant delivery device into a body via a first incision such that a portion of the target probe is disposed within the body adjacent a target location, 1022. The target probe can be any target probe of the types shown and described above. In some embodiments, for example, a distal tip of the target probe can be configured to pierce, dilate and/or displace bodily tissue to define the first incision and/or a passageway within the body.

In some embodiments, the first member of the implant delivery device can include an anchor portion, of the types shown and described above. Accordingly, in some embodiments, the inserting the target probe includes disposing the anchor portion of the implant delivery device against that body, and moving the target probe relative to the first member of the implant delivery device.

A second member of the implant delivery device is moved relative to the first member such that a distal end portion of the second member is moved from a region outside of the body to the target location within the body via a second incision, 1024. The second incision is physically distinct from the first incision. Said another way, the first incision and the second incision do not share a common boundary. The second member of the implant delivery device can be any movable member of the types shown and described above. Moreover, the distal end portion of the second member is selectively coupled to an electronic implant. Accordingly, in some embodiments, the method can optionally include decoupling the electronic implant from the distal end portion of the second member, 1026. In this manner, the electronic implant can remain within the body after the implant delivery device is removed from the body.

In some embodiments, the method optionally includes defining an insertion passageway within the body before the moving, 1028. The insertion passageway can extend from the second incision to the target location within the body and can be configured to receive the distal end portion of the second member of the implant delivery device. In some embodiments, for example, a portion of a center line of the insertion passageway can be substantially normal to a center line of the target probe. In some embodiments, the insertion passageway can be defined by the distal tip of the electronic implant and/or the distal end portion of the second member of the implant delivery device. In other embodiments, the insertion passageway can be defined by a dilator that is movably coupled to the first member of the implant delivery device.

Figure 27:
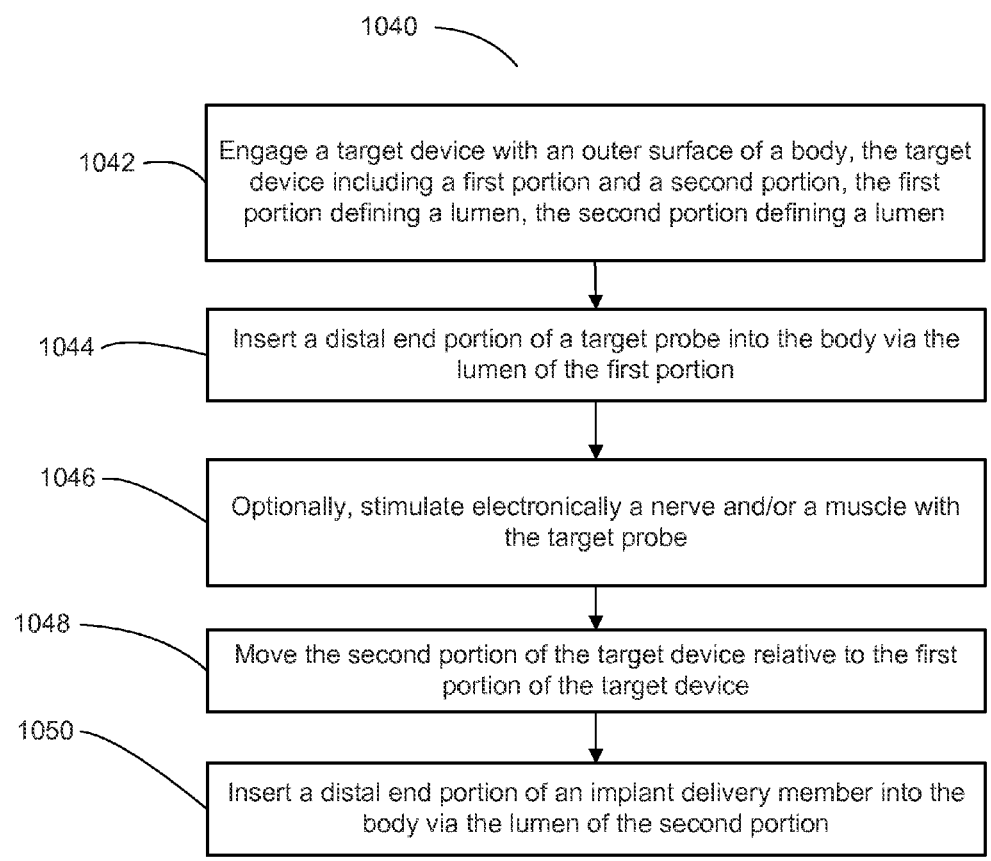

FIG. 27 is a flow chart of a method 1040 of inserting an implant into a body according to an embodiment of the invention. The method includes engaging a target device with an outer surface of a body, 1040. The target device, which can be similar to the target device 600 shown and described above with reference to FIGS. 16-18, includes a first portion and a second portion. The first portion defines a lumen, and the second portion defines a lumen. In some embodiments, for example, the engaging can include coupling a portion of the target device to the outer surface of the body. For example, in some embodiments, the target device can include a contact surface having an adhesive configured to be coupled to the skin of the body.

A distal end portion of a target probe is then inserted into the body via the lumen of the first portion, 1044. In some embodiments, for example, the target probe is inserted within the body such that the distal end portion of the target probe is adjacent a target tissue within the body. In this manner, the insertion of the target probe is guided by the target member. In some embodiments, the method optionally includes stimulating electronically a nerve and/or a muscle with the target probe after the inserting the target probe, 1046.

The second portion of the target device is moved relative to the first portion of the target device, 1048. In some embodiments, for example, the second portion of the target device is rotated relative to the first portion of the target device. Said another way, in some embodiments, the second portion of the target device is moved relative to the first portion of the target device such that an angle between the center line of the lumen of the second portion and the center line of the lumen of the first portion is adjusted.

A distal end portion of an implant delivery member is then inserted into the body via the lumen of the second portion, 1050. The implant delivery member can be any implant delivery member (also referred to herein as implant delivery tools) shown and described herein. The method can optionally include decoupling the distal end portion of the implant delivery member and the electronic implant such that the implant remains within the body.

Figure 28:
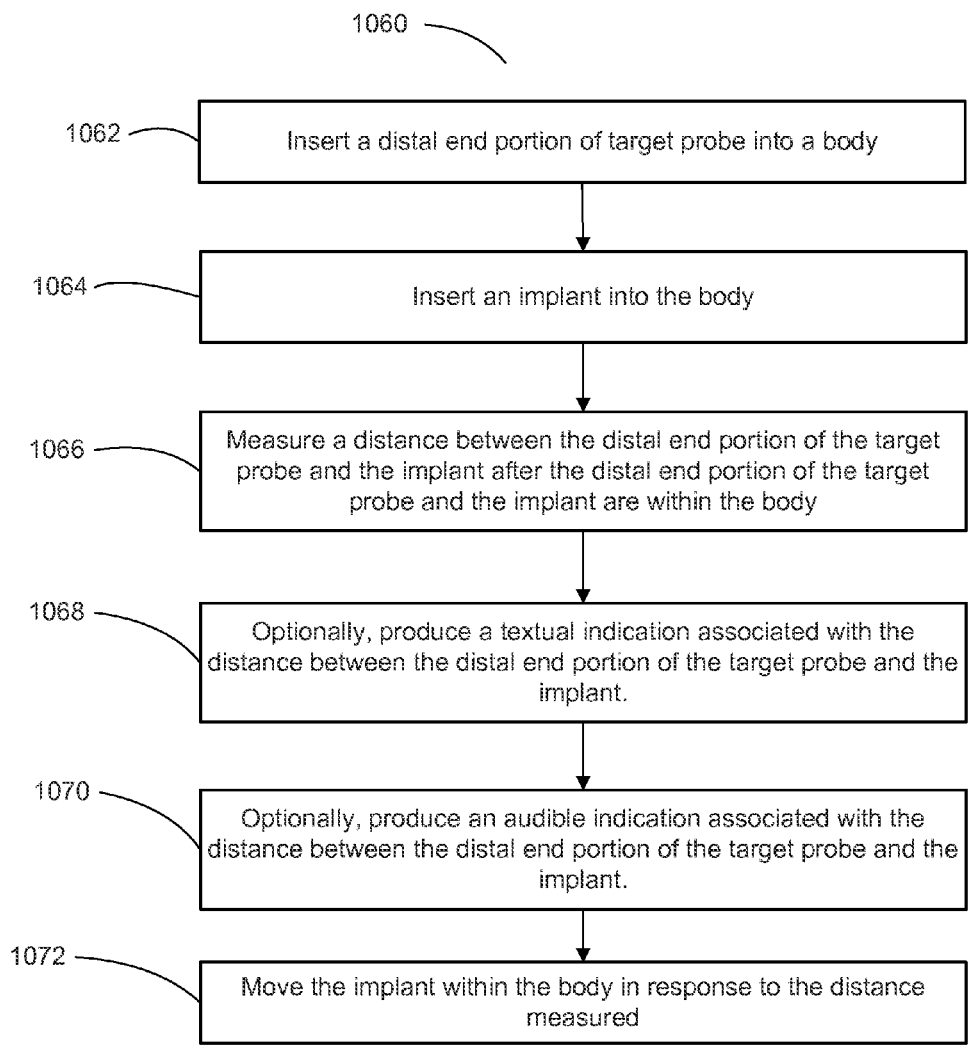

FIG. 28 is a flow chart of a method 1060 of inserting an implant into a body according to an embodiment of the invention. The method includes inserting a distal end portion of a target probe into a body, 1062. The target probe can be any target probe of the types shown and described above. For example, in some embodiments, the target probe can be an electromyogram (EMG) needle configured to be percutaneously inserted into the body to electrically stimulate and/or receive an electronic signal from the target location within the body. Accordingly, in some embodiments, the method optionally includes stimulating electronically a nerve and/or a muscle with the target probe after the inserting the target probe.

An implant is inserted into the body, 1064. The implant can be inserted using any implant insertion tool of the types shown and described herein. For example, in some embodiments, the implant can be inserted using an implant delivery device movably coupled to the target probe. In some embodiments, the implant can be inserted using an insertion tool having a distal end portion that is selectively coupled to the implant.

The implant can be any implant of the type shown and described herein. For example, in some embodiments, the implant can be an electrical implant, such as, for example, a microstimulator, an elongate implant, an electronic lead, an electrode, a power supply, an amplifier and/or a sensor. In other embodiments, the implant can be an implant that is not associated with an electronic circuit system.

A distance between the distal end portion of the target probe and the implant is measured after the distal end portion of the target probe and the implant are within the body, 1066. In some embodiments, the distance can be measured by measuring an impedance between the distal end portion of the target probe and the implant, a capacitance between the distal end portion of the target member and the implant, and/or an inductance between the distal end portion of the target member and the implant. Similarly, in some embodiments, the distance can be measured by measuring an impedance between the distal end portion of the target probe and the distal end portion of the implant delivery device, a resistance between the distal end portion of the target probe and the distal end portion of the implant delivery device, a capacitance between the distal end portion of the target member and the distal end portion of the implant delivery device, and/or an inductance between the distal end portion of the target member and the distal end portion of the implant delivery device.

In some embodiments, the distance can be measured by measuring more than one impedance value. For example, in some embodiments, the distance can be measured by measuring a first impedance and a second impedance. The first impedance is measured between a first electrode disposed at the distal end portion of the insertion member and a second electrode disposed at the distal end portion of the insertion member. The second impedance is measured between at least one of the first electrode or the second electrode and a third electrode disposed at the distal end portion of the target probe.

In some embodiments, the distance can be measured by an electronic circuit system of the types shown and described above. Moreover, in some embodiments, the method optionally includes producing a textual indication associated with the distance between the distal end portion of the target probe and the implant, 1068. Similarly, in some embodiments, the method optionally includes producing a audible indication associated with the distance between the distal end portion of the target probe and the implant, 1070.

The implant is moved within the body in response to the distance measured, 1072. In this manner, a user can move the implant from a region outside of the body to a region within the body based on the measured distance between the distal end portion of the target probe and the implant.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Thus, the breadth and scope of the invention should not be limited by any of the above-described embodiments. While the invention has been particularly shown and described with reference to specific embodiments thereof, it will be understood that various changes in form and details may be made.

For example, although many of the medical devices shown and described above include an insertion member that moves relative to a target member within a plane, in other embodiments, a medical device can include an insertion member configured to move relative to a target member in more than one plane. Said another way, in some embodiments, a medical device can include an insertion member configured to move three-dimensionally relative to a target member. Moreover, such three-dimensional movement can include rotational movement and/or translational movement.

Although the insertion member 140 is shown and described above as being rotatably coupled to the target member 110, in other embodiments, an insertion member can be removably coupled to a target member. For example, in some embodiments, a medical device can include an insertion member 140 that is rotatably and removably coupled to a target member. In this manner, after the insertion member is inserted into the body, as described above, the target member can be decoupled from the insertion member and removed from the body while the insertion member is disposed within the body.

Although the medical device 200 is shown and described above as including a coupling member 264 having an adjustable length, in other embodiments, a medical device can include any number of members having an adjustable length. For example, in some embodiments, a medical device can include a target member having an adjustable length and/or an insertion member having an adjustable length.

Although many of the medical devices shown and described above include an insertion member that is coupled to a target member either directly or via a coupling member, in other embodiments, a medical device can include an insertion member that is operatively coupled to a target member via any suitable fashion. Said another way, in some embodiments, a medical device can include an insertion member and a target member that are devoid of a mechanical coupling, but that are operatively coupled together. For example, in some embodiments, an insertion member can be electronically coupled to a target member such that the insertion member can move relative to the target member based on feedback associated with a distance between the insertion member and the target member.

Although the target members are shown and described above as being inserted into the body such that a longitudinal axis of the target member is substantially normal to the skin, in other embodiments, a target member can be inserted into the body such that a longitudinal axis of the target member is angularly offset from the skin by any suitable angle. For example, in some embodiments, the target member can be inserted into the body such that the longitudinal axis of the target member angularly offset from the skin by approximately 45 degrees. Similarly, although the insertion members are shown and described above as being inserted into the body at an angle of between 30 and 60 degrees (see e.g., FIGS. 11-13, in other embodiments, an insertion member can be inserted into the body at any suitable angle. For example, in some embodiments, an insertion member can be inserted into the body at an angle less than 30 degrees. In yet other embodiments, an insertion member can be inserted into the body at an angle greater than 60 degrees.

Although the first lumen 622 and the second lumen 648 are shown as having a constant size (i.e., diameter), in other embodiments, the first lumen 622 and/or the second lumen 648 can have a variable size. In this manner, the movement of the target probe 614 within the first lumen 622 and/or the movement of the insertion tool 640 within the second lumen 648 can be limited. For example in some embodiments, the first lumen 622 and/or the second lumen 648 can be tapered.

Although the implant insertion device 300 is shown as including a sheath 352 and a dilator 354, in other embodiments, an implant insertion device can include any number of members movably coupled to a target portion. For example, in some embodiments, an implant insertion device can include a sheath, a dilator and an implant ejector.

Similarly, although the implant insertion device 300 is shown as using the dilator 354 to mechanically move the implant 302 within the lumen 353 of the sheath 352, in other embodiments, an implant insertion device can employ any suitable mechanism to move the implant within the lumen of the sheath. For example, in some embodiments, an implant insertion device can include a pneumatic actuator to move an implant within a sheath.

Although the medical devices are shown and described above as including an implant delivery device and/or an electronic implant configured to disposed within a body, in some embodiments, a medical device can include a simulated implant delivery device and/or a simulated electronic implant. In such embodiments, for example, the simulated implant delivery device and/or the simulated electronic implant can be configured for use on a simulated target (e.g., a cadaver, a simulated body or the like). In some embodiments, for example, a simulated implant delivery device can correspond to an actual implant delivery device of the types shown and described above and can be used, for example, to train a user in the insertion of electronic implants into a body.

Although various embodiments have been described as having particular features and/or combinations of components, other embodiments are possible having a combination of any features and/or components from any of embodiments where appropriate. For example, in some embodiments, a medical device can include an target member, an insertion member, an adjustable-length coupling member, and an electronic circuit system. The adjustable-length coupling member can be similar to coupling member 264 shown and described above. The electronic circuit system can be similar to the electronic circuit system 880 shown and described above.

What is claimed is:
1. An apparatus, comprising:
an implant delivery device configured to deliver an implant into a body, the implant delivery device including:
a target member having a distal end portion configured to be disposed within the body adjacent a target location;
an insertion member movably coupled to the target member, a distal end portion of the insertion member configured to be disposed within the body and selectively coupled to the implant; and
an electronic circuit system configured to produce an electronic signal in proportion to a distance between the distal end portion of the target member and the distal end portion of the insertion member when the target member and the insertion member are disposed within the body.

2. The apparatus of claim 1, wherein:
the distal end portion of the target member is configured to be inserted percutaneously via a first incision; and
the distal end portion of the insertion member is configured to define a passageway within the body, the passageway extending from a second incision to the target location, the second incision being physically distinct from the first incision.

3. The apparatus of claim 1, wherein:
the target location includes at least one of a nerve or a muscle; and
the distal end portion of target member is configured to electrically stimulate at least one of the nerve or the muscle.

4. The apparatus of claim 1, further comprising:
the implant, the implant being an electronic implant including any one of a microstimulator, an elongate electronic implant, an electronic lead, an electrode, or a sensor.

5. The apparatus of claim 1, wherein the electronic signal is associated with at least one of an impedance between the distal end portion of the target member and the distal end portion of the insertion member, a resistance between the distal end portion of the target member and the distal end portion of the insertion member, a capacitance between the distal end portion of the target member and the distal end portion of the insertion member, and an inductance between the distal end portion of the target member and the distal end portion of the insertion member.

6. The apparatus of claim 1, wherein the electronic signal is associated with a first impedance and a second impedance, the first impedance measured between a first electrode disposed at the distal end portion of the insertion member and a second electrode disposed at the distal end portion of the insertion member, the second impedance measured between at least one of the first electrode or the second electrode and a third electrode disposed at the distal end portion of the target member.

7. The apparatus of claim 1, wherein the electronic signal is associated with an impedance between the implant and the distal end portion of the target member.

8. The apparatus of claim 1, wherein the electronic signal is associated with at least one of a textual output or an audible output.

9. An apparatus, comprising:
an implant delivery device configured to deliver an implant into a body, the implant delivery device including:
a target member having a distal end portion configured to be disposed within the body adjacent a target location;
an insertion member movably coupled to the target member, a distal end portion of the insertion member configured to be disposed within the body and selectively coupled to the implant; and
a position indicator configured to indicate a position of the distal end portion of the target member relative to the distal end portion of the insertion member when the target member and the insertion member are disposed within the body.

10. The apparatus of claim 9, wherein the position indicator includes a first portion and a second portion, the first portion coupled to the target member, the first portion including a plurality of graduated markings, the second portion coupled to the insertion member, the second portion including a pointer configured to move relative to the graduated markings of the first member.

11. The apparatus of claim 9, wherein the position indicator is configured to produce a visual indication associated with a distance between the distal end portion of the target member and the distal end portion of the insertion member.

12. The apparatus of claim 9, wherein the position indicator is configured to produce a textual indication associated with a distance between the distal end portion of the target member and the distal end portion of the insertion member.

13. The apparatus of claim 9, wherein the position indicator is configured to produce an audible indication associated with a distance between the distal end portion of the target member and the distal end portion of the insertion member.

14. The apparatus of claim 9, wherein the position indicator is configured to produce an output associated with a position of the distal end portion of the target member relative to the distal end portion of the insertion member, the output based on at least one of an impedance between the distal end portion of the target member and the distal end portion of the insertion member, a resistance between the distal end portion of the target member and the distal end portion of the insertion member, a capacitance between the distal end portion of the target member and the distal end portion of the insertion member, and an inductance between the distal end portion of the target member and the distal end portion of the insertion member.

15. A method, comprising:
inserting a distal end portion of a target probe into a body;
inserting an implant into the body;
measuring a distance between the distal end portion of the target probe and the implant after inserting the distal end portion of the target probe and inserting the implant; and
moving the implant within the body in response to the measuring.

16. The method of claim 15, wherein:
the inserting of the distal end portion of the target probe is performed using an implant delivery device via a first incision; and
the inserting of the implant is performed using the implant delivery device via a second incision, the second incision being physically distinct from the first incision.

17. The method of claim 15, wherein the measuring includes measuring at least one of an impedance between the distal end portion of the target probe and the implant, a capacitance between the distal end portion of the target member and the implant, and an inductance between the distal end portion of the target member and the implant.

18. The method of claim 15, wherein:
the inserting of the implant is performed using an implant delivery device movably coupled to the target probe, a distal end portion of the implant delivery device configured to be selectively coupled to the implant; and
the measuring includes measuring at least one of an impedance between the distal end portion of the target probe and the distal end portion of the implant delivery device, a resistance between the distal end portion of the target probe and the distal end portion of the implant delivery device, a capacitance between the distal end portion of the target member and the distal end portion of the implant delivery device, and an inductance between the distal end portion of the target member and the distal end portion of the implant delivery device.

19. The method of claim 15, wherein:
the inserting of the implant is performed using an implant delivery device movably coupled to the target probe, a distal end portion of the implant delivery device configured to be selectively coupled to the implant; and the measuring includes measuring a first impedance and a second impedance, the first impedance measured between a first electrode disposed at the distal end portion of the insertion member and a second electrode disposed at the distal end portion of the insertion member, the second impedance measured between at least one of the first electrode or the second electrode and a third electrode disposed at the distal end portion of the target probe.

20. The method of claim 15, further comprising producing a textual indication associated with the distance between the distal end portion of the target probe and the implant.

21. The method of claim 15, further comprising producing an audible indication associated with the distance between the distal end portion of the target probe and the implant.

22. A processor-readable medium storing code representing instructions to cause a processor to perform a process, the code comprising code to:

calculate a first impedance measurement, the first impedance measurement associated with an impedance between a first electrode disposed at a distal end portion of an insertion member and a second electrode disposed at the distal end portion of the insertion member when the distal end portion of the insertion member is disposed within a body;

calculate a second impedance measurement, the second impedance measurement associated with an impedance between at least one of the first electrode or the second electrode and a target probe disposed within the body;

determine a characteristic impedance of a bodily tissue based on the first impedance measurement; and determine a distance between the distal end portion of the insertion member and the target probe based on the characteristic impedance and the second impedance measurement.

23. The processor-readable medium of claim 22, wherein the code further comprises code to:

produce electronic output associated with the distance between the distal end portion of the insertion member and the target probe.

24. The processor-readable medium of claim 22, wherein the code further comprises code to:

produce an audible associated with the distance between the distal end portion of the insertion member and the target probe.

* * * * *